US010995070B2

(12) United States Patent
Slomczynska et al.

(10) Patent No.: US 10,995,070 B2
(45) Date of Patent: *May 4, 2021

(54) ACETYL-COA CARBOXYLASE MODULATORS

(71) Applicant: Monsanto Technology LLC, St. Louis, MO (US)

(72) Inventors: Urszula Slomczynska, Ballwin, MO (US); Matthew W. Dimmic, Wildwood, MO (US); William P. Haakenson, Jr., St. Louis, MO (US); Jennifer L. Bennett, St. Louis, MO (US); Barry J. Shortt, New Melle, MO (US); Christina M. Taylor, Chesterfield, MO (US); Deryck Jeremy Williams, University City, MO (US)

(73) Assignee: Monsanto Technology LLC, Saint Louis, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 16/239,946

(22) Filed: Jan. 4, 2019

(65) Prior Publication Data

US 2019/0135757 A1    May 9, 2019

Related U.S. Application Data

(63) Continuation of application No. 14/896,616, filed as application No. PCT/US2014/042267 on Jun. 13, 2014, now Pat. No. 10,207,995.

(Continued)

(51) Int. Cl.
| | | |
|---|---|---|
| *C07D 215/14* | (2006.01) |
| *A01N 25/00* | (2006.01) |
| *A61K 31/095* | (2006.01) |
| *A61K 31/04* | (2006.01) |
| *A61K 31/395* | (2006.01) |
| *A61K 31/045* | (2006.01) |
| *A61K 31/335* | (2006.01) |
| *A01N 43/42* | (2006.01) |
| *A61K 31/47* | (2006.01) |
| *A01N 43/713* | (2006.01) |
| *A01N 43/76* | (2006.01) |
| *A01N 43/78* | (2006.01) |
| *A01N 43/82* | (2006.01) |
| *A01N 57/24* | (2006.01) |

(Continued)

(52) U.S. Cl.
CPC ........... *C07D 215/14* (2013.01); *A01N 25/00* (2013.01); *A01N 35/06* (2013.01); *A01N 37/10* (2013.01); *A01N 37/22* (2013.01); *A01N 41/10* (2013.01); *A01N 41/12* (2013.01); *A01N 43/16* (2013.01); *A01N 43/18* (2013.01); *A01N 43/42* (2013.01); *A01N 43/54* (2013.01); *A01N 43/60* (2013.01); *A01N 43/713* (2013.01); *A01N 43/76* (2013.01); *A01N 43/78* (2013.01); *A01N 43/82* (2013.01); *A01N 43/84* (2013.01); *A01N 57/20* (2013.01); *A01N 57/24* (2013.01); *A01N 63/00* (2013.01); *A01N 63/30* (2020.01); *A01N 65/08* (2013.01); *A61K 31/04* (2013.01); *A61K 31/045* (2013.01); *A61K 31/095* (2013.01); *A61K 31/335* (2013.01); *A61K 31/395* (2013.01); *A61K 31/47* (2013.01); *C07D 215/18* (2013.01); *C07D 215/26* (2013.01); *C07D 215/36* (2013.01); *C07D 257/04* (2013.01); *C07D 409/04* (2013.01)

(58) Field of Classification Search
CPC .. C07D 215/14; C07D 215/18; C07D 215/26; C07D 215/36; C07D 409/04; C07D 257/04; A01N 63/30; A01N 25/00; A01N 35/06; A01N 37/10; A01N 37/22; A01N 41/10; A01N 41/12; A01N 43/16; A01N 43/18; A01N 43/54; A01N 43/60; A01N 43/84; A01N 57/20; A01N 63/00; A01N 65/08; A01N 43/713; A01N 43/76; A01N 43/78; A01N 43/82; A01N 57/24; A01N 43/42; A61K 31/095; A61K 31/04; A61K 31/395; A61K 31/045; A61K 31/335; A61K 31/47

See application file for complete search history.

(56) References Cited

U.S. PATENT DOCUMENTS

| | | | | |
|---|---|---|---|---|
| 4,465,017 A ‡ | 8/1984 | Simmons | ................ | A01C 1/06 118/41 |
| 4,759,945 A ‡ | 7/1988 | Nemecek | ................ | A01C 1/08 427/34 |

(Continued)

FOREIGN PATENT DOCUMENTS

| | | | |
|---|---|---|---|
| WO | WO-1998034115 A1 ‡ | 8/1998 | |
| WO | WO-1999520892 A1 ‡ | 10/1999 | |

(Continued)

OTHER PUBLICATIONS

PubChem Substance Summary for CID 17391770 Deposit Date Nov. 13, 2007 (Nov. 13, 2007), pp. 1-3. (Year: 2007).*

(Continued)

*Primary Examiner* — John Pak
*Assistant Examiner* — Andriae M Holt
(74) *Attorney, Agent, or Firm* — Stinson LLP; Lawrence M. Lavin, Jr.

(57) ABSTRACT

Provided herein are compounds that exhibit activity as acetyl-CoA carboxylase modulators (e.g., inhibitors) and are useful, for example, in methods for the control of fungal pathogens in plants.

29 Claims, No Drawings

Related U.S. Application Data

(60) Provisional application No. 61/834,585, filed on Jun. 13, 2013.

(51) Int. Cl.

| *A01N 63/30* | (2020.01) |
| *C07D 257/04* | (2006.01) |
| *A01N 35/06* | (2006.01) |
| *A01N 37/10* | (2006.01) |
| *A01N 37/22* | (2006.01) |
| *A01N 41/10* | (2006.01) |
| *A01N 41/12* | (2006.01) |
| *A01N 43/16* | (2006.01) |
| *A01N 43/18* | (2006.01) |
| *A01N 43/54* | (2006.01) |
| *A01N 43/60* | (2006.01) |
| *A01N 43/84* | (2006.01) |
| *A01N 57/20* | (2006.01) |
| *A01N 63/00* | (2020.01) |
| *A01N 65/08* | (2009.01) |
| *C07D 215/18* | (2006.01) |
| *C07D 215/26* | (2006.01) |
| *C07D 215/36* | (2006.01) |
| *C07D 409/04* | (2006.01) |

(56) References Cited

U.S. PATENT DOCUMENTS

| 5,080,925 | A | ‡ | 1/1992 | Kouno | B01J 13/08 |
| | | | | | 264/5 |
| 5,107,787 | A | ‡ | 4/1992 | Kouno | B01J 13/08 |
| | | | | | 118/23 |
| 5,240,940 | A | * | 8/1993 | Arnold | C07D 405/12 |
| | | | | | 514/312 |
| 5,389,399 | A | ‡ | 2/1995 | Bazin | A01C 1/06 |
| | | | | | 118/19 |
| 5,554,445 | A | ‡ | 9/1996 | Struszczyk | A01N 43/16 |
| | | | | | 427/21 |
| 5,891,246 | A | ‡ | 4/1999 | Lund | A01C 1/06 |
| | | | | | 118/13 |
| 5,918,413 | A | ‡ | 7/1999 | Otani | A01C 1/06 |
| | | | | | 442/16 |
| 10,207,995 | B2 | * | 2/2019 | Slomczynska | A01N 43/42 |
| 2006/0128702 | A1 | ‡ | 6/2006 | Pal | C07D 215/38 |
| | | | | | 514/23 |
| 2007/0015799 | A1 | ‡ | 1/2007 | Ashton | A61K 31/10 |
| | | | | | 514/34 |
| 2007/0027190 | A1 | ‡ | 2/2007 | Moir | A61K 31/44 |
| | | | | | 514/34 |
| 2008/0200461 | A1 | ‡ | 8/2008 | Anderson | C07D 275/03 |
| | | | | | 514/23 |
| 2008/0255150 | A1 | ‡ | 10/2008 | Luker | C07D 295/185 |
| | | | | | 514/25 |
| 2008/0300303 | A1 | ‡ | 12/2008 | Huse | A61K 31/22 |
| | | | | | 514/51 |
| 2009/0048311 | A1 | ‡ | 2/2009 | Williams | A01N 43/76 |
| | | | | | 514/36 |
| 2009/0306133 | A1 | ‡ | 12/2009 | Blomberg | C07D 215/36 |
| | | | | | 514/31 |
| 2011/0028320 | A1 | ‡ | 2/2011 | Slomczynska | C07D 413/04 |
| | | | | | 504/11 |
| 2011/0046110 | A1 | * | 2/2011 | Vu | A61P 19/02 |
| | | | | | 514/210.21 |
| 2011/0275645 | A1 | ‡ | 11/2011 | Desai | A61K 31/15 |
| | | | | | 514/25 |
| 2012/0252801 | A1 | ‡ | 10/2012 | Bardiot | C07D 265/32 |
| | | | | | 514/23 |
| 2013/0058980 | A1 | ‡ | 3/2013 | Desai | A61K 31/15 |
| | | | | | 424/27 |

FOREIGN PATENT DOCUMENTS

| WO | WO-2004064837 A1 | ‡ | 8/2004 |
| WO | WO-2004101506 A1 | ‡ | 11/2004 |
| WO | WO-2007124544 A1 | ‡ | 8/2007 |
| WO | WO-2007124545 A1 | ‡ | 11/2007 |
| WO | WO-2012030887 A1 | ‡ | 3/2012 |
| WO | WO-2013037735- | ‡ | 3/2013 |

OTHER PUBLICATIONS

Reichenbach H, et al. "Discovery of a new antifungal mechanism of action, soraphen: an almost-success story," 1994, In JH Walsdorff, ed, Scientific Annual Report. Gesellschaft für Biotechnologische Forschung mbH, Braunschweig, Germany, pp. 5-22.‡

"Current Methods in Medicinal Chemistry and Biological Physics" vol. 2 (2008) pp. 187-214.‡

Fedotov et al., "Cyclization of Substituted (2-Pyridylthio)Phenylacetic Acids and Chromaticity of Mesoionic Thiazolo[3,2-a]Pyridinium-3-Olates," 2011, Chem Hetero Comp, 45/5:622-630.‡

Pakdaman, B.S., et al., "An in vitro Study on the Possibility of Rapeseed White Stem Rot Disease Control Through the Application of Prevalent Herbicides and Trichoderma Species," 2006, Pak J Biol Sci, 10:7-12.‡

Pakdaman, B.S. et al., "Cellular Membranes as the Sites for the Antifungal Activity of the Herbicide Sethoxydim," 2007, Pak J Biol Sci 10:2480-2484.‡

Rodinovskaya et al., "One-Pot Synthesis of Diverse 4-Di(tri)Fluoromethyl-3-Cyanopyridine-2(1H)Thiones and Their Utilities in the Cascade Synthesis of Annulated Heterocycles," 2008, J Comb Chem, 10:313-322.‡

Tong L., et al., "Acetyl-Coenzyme A Carboxylases: Versatile Targets for Drug Discovery," 2006, J Cell Biochem, 99:1476-1488.‡

Biotechnology: Pharmaceutical Aspects, "Prodrugs: Challenges and Rewards Part 2", V. Stella et al. Editors, vol. V (2007) pp. 3-33, 41 pages.‡

Pubchem CID-1035635 Create Date: Jul. 10, 2005 (Jul. 10, 2005) p. 1.‡

Pubchem CID 16325401 Deposit Date Jul. 30, 2007 (Jul. 30, 2007) pp. 1-4.‡

Pubchem Substance Summary for CID 17391770 Deposit Date Nov. 13, 2007 (Nov. 13, 2007), pp. 1-4.‡

International Search Report issued in PCT/US2014/42265, dated Oct. 10, 2014, 6 pages.‡

Gutierrez, M., Antifungal activity of tetrahydroquinolines against some phytopathogenic fungi, 2012, Zeitschrif Fuer Naturforschung, C: Journal of Biosciences, vol. 67 (11/12), pp. 551-556.‡

El-Dine, et al., Potential fungicidal and bactericidal agents, Synthesis of Certain 4-(2-amino-1,3,4-thiadiazol-5-yl)quinolines, 1979, Pharmazie, Abstract, STN, HCAPlus, 2 pages, 118-119.‡

Ling, L.L., et al., "Identification and Characterization of Inhibitors of Bacterial Enoyl-Acyl Carrier Protein Reductase," 2004, Antimicrobial Agents and Chemotherapy, 1541-1547, 7 pages.

\* cited by examiner
‡ imported from a related application

ACETYL-COA CARBOXYLASE MODULATORS

REFERENCE TO RELATED APPLICATIONS

This application is a continuation of U.S. patent application Ser. No. 14/896,616, filed Dec. 7, 2015, which is the U.S. National Stage of International Patent Application No. PCT/US2014/042267, filed Jun. 13, 2014, which claims the benefit of U.S. Provisional Application Ser. No. 61/834,585, filed Jun. 13, 2013, the entire contents of which are incorporated herein by reference.

FIELD

Provided herein are compounds that exhibit activity as acetyl-CoA carboxylase modulators (e.g., inhibitors) and are useful, for example, in methods for the control of fungal pathogens and diseases caused by fungal pathogens in plants.

BACKGROUND

Acetyl-CoA carboxylase ("ACCase") is an essential catalyst for the rate-limiting step of fatty acid biosynthesis in both eukaryotes and prokaryotes. Phytopathogenic fungi can infect crop plants either in the field or after harvesting, resulting in considerable economic losses to farmers and producers worldwide. In addition to the agricultural impact, when food and feed contaminated with fungi or the toxins they produce are ingested by humans or livestock, a number of debilitating diseases or death can occur. Approximately 10,000 species of fungi are known to damage crops and affect quality and yield. Crop rotation, breeding of resistant cultivars, the application of agrochemicals and combinations of these strategies is commonly employed to stem the spread of fungal pathogens and the diseases they cause. Additional chemistry and methods of using such as a modulator for ACCase or to control fungi are important for, among other things, protection in agriculture.

For example, the rapid onset of resistance to chemical fungicides has often lowered the efficacy of some chemical fungicides. This threat, as well as emergence and spread of additional fungal diseases, accentuates the need for new means of fungal control.

SUMMARY

In one aspect, therefore, the present disclosure is directed to a compound of Formula I or a salt thereof,

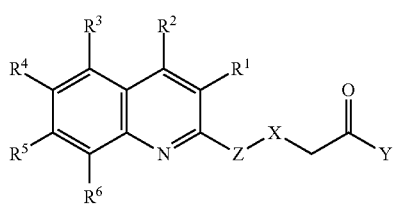

Formula I wherein $R^1$ is selected from the group consisting of hydrogen, halogen, alkyl, alkoxy, haloalkyl, and haloalkoxy; $R^2$ is selected from the group consisting of aryl and heteroaryl, each of which may be optionally independently substituted with one or more substituents selected from the group consisting of halogen, OH, CN, alkyl, alkoxy, haloalkyl, haloalkoxy, alkenyl, $C_1$ to $C_4$ hydroxyalkyl, $N(R^7R^8)$, and $NR^9C(O)R^{10}$, wherein $R^7$ and $R^8$ are each independently selected from the group consisting of hydrogen and alkyl, and wherein $R^9$ is selected from the group consisting of hydrogen and alkyl and $R^{10}$ is alkyl; $R^3$, $R^4$, $R^5$, and $R^6$ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl; X is selected from the group consisting of a bond, $CH_2$, O, S, NH, and $N(CH_3)$; Y is selected from the group consisting of OH, $NH_2$, N(H)OH, $N(CH_3)OH$, and $N(R^7R^8)$, wherein $R^7$ and $R^8$ are each independently selected from the group consisting of hydrogen, alkyl, and hydroxyalkyl; and Z is selected from the group consisting of aryl and heteroaryl, each of which may be optionally independently substituted with one or more substituents selected from the group consisting of halogen, alkyl, alkoxy, haloalkyl, haloalkoxy, $C_1$ to $C_4$ hydroxyalkyl, CN, and C(H)O.

In another aspect, the present disclosure is directed to a compound of Formula II or a salt thereof,

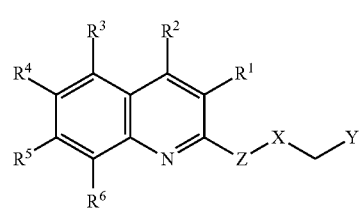

Formula II wherein $R^1$ is selected from the group consisting of hydrogen, halogen, alkyl, alkoxy, haloalkyl, and haloalkoxy; $R^2$ is selected from the group consisting of aryl and heteroaryl, each of which may be optionally independently substituted with one or more substituents selected from the group consisting of halogen, OH, CN, alkyl, alkoxy, haloalkyl, haloalkoxy, alkenyl, $C_1$ to $C_4$ hydroxyalkyl, $N(R^7R^8)$, and $NR^9C(O)R^{10}$, wherein $R^7$ and $R^8$ are each independently selected from the group consisting of hydrogen and alkyl, and wherein $R^9$ is selected from the group consisting of hydrogen and alkyl and $R^{10}$ is alkyl; $R^3$, $R^4$, $R^5$, and $R^6$ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl; X is selected from the group consisting of a bond, $CH_2$, O, S, NH, and $N(CH_3)$; Y is selected from the group consisting of hydrogen, a prodrug of a carboxylic acid and a carboxylic acid isostere; and Z is selected from the group consisting of aryl and heteroaryl, each of which may be optionally independently substituted with one or more substituents selected from the group consisting of halogen, alkyl, alkoxy, haloalkyl, haloalkoxy, $C_1$ to $C_4$ hydroxyalkyl, CN, and C(H)O. In some embodiments, when $R^2$ is phenyl, Z is phenyl, and Y is $C(O)OCH_2CH_3$, $R^4$ is other than halogen.

In another aspect, the present disclosure is directed to a compound of Formula III or a salt thereof,

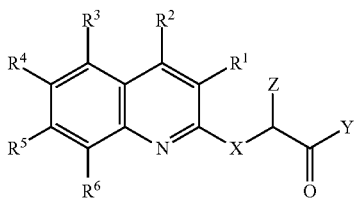

Formula III wherein R¹ is selected from the group consisting of hydrogen, halogen, alkyl, alkoxy, haloalkyl, and haloalkoxy; R² is selected from the group consisting of aryl and heteroaryl, each of which may be optionally independently substituted with one or more substituents selected from the group consisting of halogen, OH, CN, alkyl, alkoxy, haloalkyl, haloalkoxy, alkenyl, $C_1$ to $C_4$ hydroxyalkyl, $N(R^7R^8)$, and $NR^9C(O)R^{10}$, wherein $R^7$ and $R^8$ are each independently selected from the group consisting of hydrogen and alkyl, and wherein $R^9$ is selected from the group consisting of hydrogen and alkyl and $R^{10}$ is alkyl; $R^3$, $R^4$, $R^5$, and $R^6$ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl; X is selected from the group consisting of $CH_2$, O, S, NH, and $N(CH_3)$; Y is selected from the group consisting of OH, $NH_2$, N(H)OH, $N(CH_3)OH$, and $N(R^7R^8)$, wherein $R^7$ and $R^8$ are each independently selected from the group consisting of hydrogen, alkyl, and hydroxyalkyl; and Z is selected from the group consisting of hydrogen, alkyl, haloalkyl, and cycloalkyl.

In another aspect, the present disclosure is directed to a compound of Formula IV or a salt thereof,

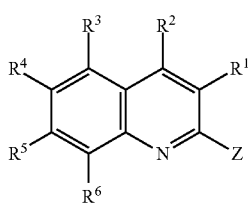

Formula IV wherein R¹ is selected from the group consisting of hydrogen, halogen, alkyl, alkoxy, haloalkyl, and haloalkoxy; R² is selected from the group consisting of aryl and heteroaryl, each of which may be optionally independently substituted with one or more substituents selected from the group consisting of halogen, OH, CN, alkyl, alkoxy, haloalkyl, haloalkoxy, alkenyl, $C_1$ to $C_4$ hydroxyalkyl, $N(R^7R^8)$, and $NR^9C(O)R^{10}$, wherein $R^7$ and $R^8$ are each independently selected from the group consisting of hydrogen and alkyl, and wherein $R^9$ is selected from the group consisting of hydrogen and alkyl and $R^{10}$ is alkyl; $R^3$, $R^4$, $R^5$, and $R^6$ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl; and Z is selected from the group consisting of aryl and heteroaryl, each of which may be optionally independently substituted with one or more substituents selected from the group consisting of halogen, alkyl, alkoxy, haloalkyl, and haloalkoxy, $C_1$ to $C_4$ hydroxyalkyl, CN, and C(H)O.

Another aspect of the present disclosure is directed to a compound selected from the group consisting of: 2-(4-(4-phenylquinolin-2-yl)phenoxy)acetamide, or a salt thereof, 2-(4-(4-phenylquinolin-2-yl)phenoxy)acetic acid, or a salt thereof, 2-(4-(8-methoxy-4-phenylquinolin-2-yl)phenoxy) acetamide, or a salt thereof, 2-(4-(8-ethyl-4-phenylquinolin-2-yl)phenoxy)acetamide, or a salt thereof, 2-(4-(6-chloro-4-phenylquinolin-2-yl)phenoxy)-N-(2-hydroxyethyl) acetamide, or a salt thereof, 2-(5-(3-chloro-4-phenylquinolin-2-yl)thiophen-2-yl)acetamide, or a salt thereof, 2-(5-(3-chloro-4-phenylquinolin-2-yl)thiophen-2-yl) acetic acid, or a salt thereof, 2-(5-(4-phenylquinolin-2-yl)thiophen-2-yl)acetamide, or a salt thereof, 2-(5-(4-phenylquinolin-2-yl)thiophen-2-yl)acetic acid, or a salt thereof, 2-(5-(8-methoxy-4-phenylquinolin-2-yl)thiophen-2-yl)acetamide, or a salt thereof, 2-(5-(8-ethyl-4-phenylquinolin-2-yl)thiophen-2-yl)acetamide, or a salt thereof, 2-(4-((1H-tetrazol-5-yl)methoxy)phenyl)-4-phenylquinoline, or a salt thereof, ((4-(4-phenylquinolin-2-yl)phenoxy)methyl)phosphonic acid, or a salt thereof, ((4-(4-phenylquinolin-2-yl) phenoxy)methyl)phosphinic acid, or a salt thereof, (4-(4-phenylquinolin-2-yl)phenoxy)methanesulfonic acid, or a salt thereof, (4-(4-phenylquinolin-2-yl)phenoxy)methanesulfonamide, or a salt thereof, N-(methylsulfonyl)-2-(4-(4-phenylquinolin-2-yl)phenoxy)acetamide, or a salt thereof, 5-((4-(4-phenylquinolin-2-yl)phenoxy)methyl)thiazolidine-2,4-dione, or a salt thereof, 5-((4-(4-phenylquinolin-2-yl) phenoxy)methyl)oxazolidine-2,4-dione, or a salt thereof, 3-((4-(4-phenylquinolin-2-yl)phenoxy)methyl)-1,2,4-oxadiazol-5 (4H)-one, or a salt thereof, 2-(5-((1H-tetrazol-5-yl) methyl)thiophen-2-yl)-4-phenylquinoline, or a salt thereof, (((5-(4-phenylquinolin-2-yl)thiophen-2-yl)methyl)phosphonic acid, or a salt thereof, (((5-(4-phenylquinolin-2-yl)thiophen-2-yl)methyl)phosphinic acid, or a salt thereof, ((5-(4-phenylquinolin-2-yl)thiophen-2-yl)methanesulfonic acid, or a salt thereof, ((5-(4-phenylquinolin-2-yl)thiophen-2-yl) methanesulfonamide, or a salt thereof, N-(methylsulfonyl)-2-(5-(4-phenylquinolin-2-yl)thiophen-2-yl)acetamide, or a salt thereof, 5-(((5-(4-phenylquinolin-2-yl)thiophen-2-yl) methyl)thiazolidine-2,4-dione, or a salt thereof, 5-(((5-(4-phenylquinolin-2-yl)thiophen-2-yl)methyl)oxazolidine-2,4-dione, or a salt thereof, 3-(((5-(4-phenylquinolin-2-yl) thiophen-2-yl)methyl)-1,2,4-oxadiazol-5(4H)-one, or a salt thereof, methyl 2-(4-(4-phenylquinolin-2-yl)phenoxy)acetate, or a salt thereof, methyl 2-(5-(4-phenylquinolin-2-yl) thiophen-2-yl)acetate, or a salt thereof, methyl 2-(5-(3-chloro-4-phenylquinolin-2-yl)thiophen-2-yl)acetate, or a salt thereof, 2-((7-methoxy-4-phenylquinolin-2-yl)thio)propanamide, or a salt thereof, 2-(4-methoxyphenyl)-4-phenylquinoline, or a salt thereof, and 2-(3,4-dimethoxyphenyl)-4-phenylquinoline, or a salt thereof.

Another aspect of the present disclosure is generally related to a method of controlling fungal pathogens comprising administering to a plant, a seed or soil a composition comprising an effective amount of a compound as described herein.

Another aspect of the present disclosure is generally related to a method for modulating ACCase in a biological organism comprising administering to the biological organism a composition comprising an effective amount of a compound as described herein.

Another aspect of the present disclosure is generally related to a composition comprising a compound as described herein.

Another aspect of the present disclosure is generally related to a seed comprising a coating comprising a compound or a composition as described herein.

Other objects and features will be in part apparent and in part pointed out hereinafter.

DETAILED DESCRIPTION

Described herein are compounds that exhibit activity as acetyl-CoA carboxylase (ACCase) modulators. The compounds described herein may be used, for example, in the preparation of compositions and in accordance with methods for control of fungal pathogens, as set forth in detail below.

For example, in one embodiment, the compound is a compound of Formula I or a salt thereof,

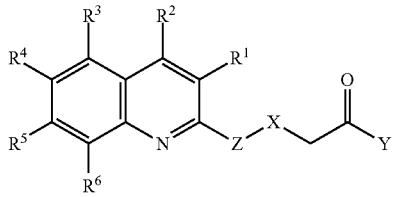

Formula I wherein
$R^1$ is selected from the group consisting of hydrogen, halogen, alkyl, alkoxy, haloalkyl, and haloalkoxy;
$R^2$ is selected from the group consisting of aryl and heteroaryl, each of which may be optionally independently substituted with one or more substituents selected from the group consisting of halogen, OH, CN, alkyl, alkoxy, haloalkyl, haloalkoxy, alkenyl, $C_1$ to $C_4$ hydroxyalkyl, $N(R^7R^8)$, and $NR^9C(O)R^{10}$, wherein $R^7$ and $R^8$ are each independently selected from the group consisting of hydrogen and alkyl, and wherein $R^9$ is selected from the group consisting of hydrogen and alkyl and $R^{10}$ is alkyl;
$R^3$, $R^4$, $R^5$, and $R^6$ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl and wherein $R^9$ is selected from the group consisting of hydrogen and alkyl and $R^{10}$ and $R^{11}$ are alkyl;
X is selected from the group consisting of a bond, $CH_2$, O, S, NH, and $N(CH_3)$;
Y is selected from the group consisting of OH, $NH_2$, N(H)OH, $N(CH_3)OH$, and $N(R^7R^8)$ wherein $R^7$ and $R^8$ are each independently selected from the group consisting of hydrogen, alkyl, and hydroxyalkyl; and
Z is selected from the group consisting of aryl and heteroaryl, each of which may be optionally independently substituted with one or more substituents selected from the group consisting of halogen, alkyl, alkoxy, haloalkyl, haloalkoxy, $C_1$ to $C_4$ hydroxyalkyl, CN, and C(H)O.

In some embodiments, $R^2$ is selected from the group consisting of aryl and heteroaryl, each of which may be optionally independently substituted with one or more substituents selected from the group consisting of halogen, OH, $CH_3$, $OCH_3$, $CF_3$, $OCF_3$, and CN. For example, in some embodiments, $R^2$ is phenyl.

In some embodiments, Z is selected from the group consisting of aryl and heteroaryl, each of which may be optionally independently substituted with one or more substituents selected from the group consisting of halogen, $CH_3$, $OCH_3$, $CF_3$, $OCF_3$, CN, and C(H)O.

For example, in some embodiments, Z is selected from the group consisting of phenyl and thienyl. In some embodiments, Z is phenyl. In other embodiments, Z is thienyl.

For example, the compound of Formula I may be a compound of Formula Ia or a salt thereof,

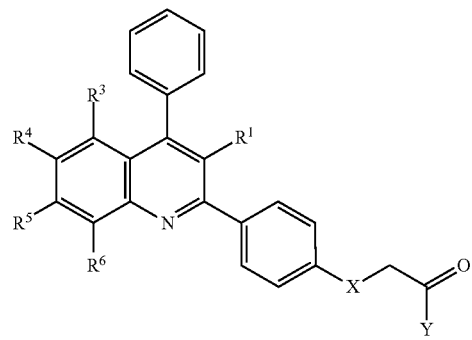

Formula Ia wherein
$R^1$ is selected from the group consisting of hydrogen, halogen, alkyl, alkoxy, haloalkyl, and haloalkoxy;
$R^3$, $R^4$, $R^5$, and $R^6$ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl;
X is selected from the group consisting of $CH_2$, O, S, NH, and $N(CH_3)$; and
Y is selected from the group consisting of OH, $NH_2$, N(H)OH, $N(CH_3)OH$, and $N(R^7R^8)$, wherein $R^7$ and $R^8$ are each independently selected from the group consisting of hydrogen, alkyl, and hydroxyalkyl.

Alternatively, the compound of Formula I may be a compound of Formula Ib or a salt thereof,

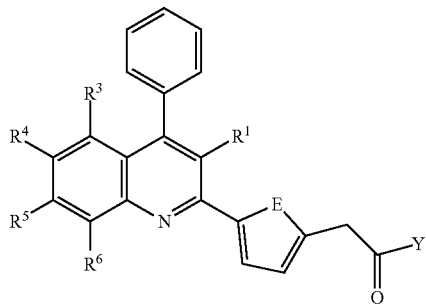

Formula Ib wherein
$R^1$ is selected from the group consisting of hydrogen, halogen, alkyl, alkoxy, haloalkyl, and haloalkoxy;
$R^3$, $R^4$, $R^5$, and $R^6$ are each independently selected from the group consisting of hydrogen, halogen, OH, alkyl, alkoxy, haloalkyl, haloalkoxy, $C_1$ to $C_4$ hydroxyalkyl, $N(R^7R^8)$, and $NR^9C(O)R^{10}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl;

Y is selected from the group consisting of OH, $NH_2$, N(H)OH, $N(CH_3)OH$, and $N(R^7R^8)$, wherein $R^7$ and $R^8$ are each independently selected from the group consisting of hydrogen, alkyl, and hydroxyalkyl; and E is selected from the group consisting of S, O, and $N(CH_3)$.

In some embodiments, the compound is a compound of formula Ib wherein E is S. In other embodiments, E is O. In still further embodiments, E is $N(CH_3)$.

In some embodiments, the compound is a compound of Formula I, Ia, or Ib wherein $R^1$ is selected from the group consisting of hydrogen, halogen, $CH_3$, $OCH_3$, $CF_3$, and $OCF_3$. In some embodiments, $R^1$ is hydrogen. In other embodiments, $R^1$ is halogen.

In some embodiments, the compound is a compound of Formula I, Ia, or Ib wherein $R^3$, $R^4$, $R^5$, and $R^6$ are each independently selected from the group consisting of hydrogen, halogen, OH, $CH_3$, $OCH_3$, $CF_3$, and $OCF_3$. For example, in some embodiments, $R^3$, $R^4$, $R^5$, and $R^6$ are each hydrogen.

In some embodiments, the compound is a compound of Formula I or Ia wherein X is selected from the group consisting of a bond and S. For example, in some embodiments, X is a bond. In other embodiments, X is S.

In some embodiments, the compound is a compound of Formula I, Ia, or Ib wherein Y is selected from the group consisting of OH and $NH_2$. In some embodiments, Y is OH. In other embodiments, Y is $NH_2$.

In another embodiment, the compound is a compound of Formula II or a salt thereof,

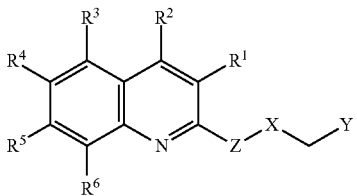

Formula II wherein $R^1$ is selected from the group consisting of hydrogen, halogen, alkyl, alkoxy, haloalkyl, and haloalkoxy;

$R^2$ is selected from the group consisting of aryl and heteroaryl, each of which may be optionally independently substituted with one or more substituents selected from the group consisting of halogen, OH, CN, alkyl, alkoxy, haloalkyl, haloalkoxy, alkenyl, $C_1$ to $C_4$ hydroxyalkyl, $N(R^7R^8)$, and $NR^9C(O)R^{10}$, wherein $R^7$ and $R^8$ are each independently selected from the group consisting of hydrogen and alkyl, and wherein $R^9$ is selected from the group consisting of hydrogen and alkyl and $R^{10}$ is alkyl;

$R^3$, $R^4$, $R^5$, and $R^6$ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl;

X is selected from the group consisting of a bond, $CH_2$, O, S, NH, and $N(CH_3)$;

Y is selected from the group consisting of hydrogen, a prodrug of a carboxylic acid and a carboxylic acid isostere; and Z is selected from the group consisting of aryl and heteroaryl, each of which may be optionally independently substituted with one or more substituents selected from the group consisting of halogen, alkyl, alkoxy, haloalkyl, and haloalkoxy, $C_1$ to $C_4$ hydroxyalkyl, CN, and C(H)O.

In some embodiments, when $R^2$ is phenyl, Z is phenyl, and Y is $C(O)OCH_2CH_3$, $R^4$ is other than halogen.

In some embodiments, $R^2$ is selected from the group consisting of aryl and heteroaryl, each of which may be optionally independently substituted with one or more substituents selected from the group consisting of halogen, OH, $CH_3$, $OCH_3$, $CF_3$, $OCF_3$, and CN. For example, in some embodiments, $R^2$ is phenyl.

In some embodiments, Z is selected from the group consisting of aryl and heteroaryl, each of which may be optionally independently substituted with one or more substituents selected from the group consisting of halogen, $CH_3$, $OCH_3$, $CF_3$, $OCF_3$, CN, and C(H)O.

For example, in some embodiments, Z is selected from the group consisting of phenyl and thienyl. In some embodiments, Z is phenyl. In other embodiments, Z is thienyl.

For example, the compound of Formula II may be a compound of Formula IIa or a salt thereof,

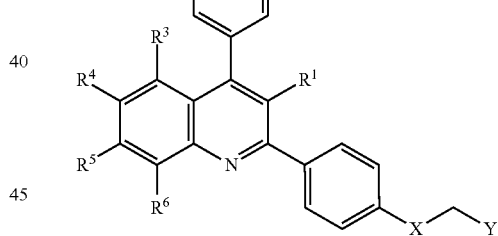

Formula IIa wherein $R^1$ is selected from the group consisting of hydrogen, halogen, alkyl, alkoxy, haloalkyl, and haloalkoxy;

$R^3$, $R^4$, $R^5$, and $R^6$ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl;

X is selected from the group consisting of $CH_2$, O, S, NH, and $N(CH_3)$; and

Y is selected from the group consisting of hydrogen and a carboxylic acid isostere.

Alternatively, the compound of Formula II may be a compound of Formula IIb or a salt thereof, Formula IIb

[Chemical structure of Formula IIb: quinoline with R³, R⁴, R⁵, R⁶ substituents on benzene ring, R¹ on pyridine ring, 4-phenyl group, and 2-position bearing a 5-membered heterocycle (E) with CH₂-Y substituent]

wherein

R¹ is selected from the group consisting of hydrogen, halogen, alkyl, alkoxy, haloalkyl, and haloalkoxy;

R³, R⁴, R⁵, and R⁶ are each independently selected from the group consisting of hydrogen, halogen, OH, alkyl, alkoxy, haloalkyl, haloalkoxy, $C_1$ to $C_4$ hydroxyalkyl, N(R⁷R⁸) NR⁹C(O)R¹⁰, and C(O)R¹¹, wherein R⁷ and R⁸ are each independently selected from the group consisting of hydrogen and alkyl, and wherein R⁹ is selected from the group consisting of hydrogen and alkyl and R¹⁰ and R¹¹ are alkyl;

Y is a carboxylic acid isostere; and

E is selected from the group consisting of S, O, and N(CH₃).

In another embodiment, the compound of Formula II may be a compound of Formula IIc or a salt thereof, Formula IIc

[Chemical structure of Formula IIc: quinoline with R³, R⁴, R⁵, R⁶ substituents, R¹ substituent, 4-phenyl group, and 2-(4-substituted phenyl) group with X-CH₂-Y]

wherein

R¹ is selected from the group consisting of hydrogen, halogen, alkyl, alkoxy, haloalkyl, and haloalkoxy;

R³, R⁴, R⁵, and R⁶ are each independently selected from the group consisting of hydrogen, halogen, OH, alkyl, alkoxy, haloalkyl, haloalkoxy, $C_1$ to $C_4$ hydroxyalkyl, N(R⁷R⁸), NR⁹C(O)R¹⁰, and C(O)R¹¹, wherein R⁷ and R⁸ are each independently selected from the group consisting of hydrogen and alkyl, and wherein R⁹ is selected from the group consisting of hydrogen and alkyl and R¹⁰ and R¹¹ are alkyl;

X is selected from the group consisting of CH₂, O, S, NH, and N(CH₃); and

Y is selected from the group consisting of hydrogen and a prodrug of carboxylic acid.

In some embodiments, when Y is C(O)OCH₂CH₃, R⁴ is other than halogen.

In a further embodiment, the compound of Formula II may be a compound of Formula IId or a salt thereof, Formula IId

[Chemical structure of Formula IId: quinoline with R³, R⁴, R⁵, R⁶ substituents, R¹ substituent, 4-phenyl group, and 2-position bearing a 5-membered heterocycle (E) with CH₂-Y substituent]

wherein

R¹ is selected from the group consisting of hydrogen, halogen, alkyl, alkoxy, haloalkyl, and haloalkoxy;

R³, R⁴, R⁵, and R⁶ are each independently selected from the group consisting of hydrogen, halogen, OH, alkyl, alkoxy, haloalkyl, haloalkoxy, $C_1$ to $C_4$ hydroxyalkyl, N(R⁷R⁸), NR⁹C(O)R¹⁰, and C(O)R¹¹, wherein R⁷ and R⁸ are each independently selected from the group consisting of hydrogen and alkyl, and wherein R⁹ is selected from the group consisting of hydrogen and alkyl and R¹⁰ and R¹¹ are alkyl;

Y is a prodrug of carboxlic acid; and

E is selected from the group consisting of S, O, and N(CH₃).

In some embodiments, the compound is a compound of formula IIb or IId wherein E is S. In other embodiments, E is O. In still further embodiments, E is N(CH₃).

In some embodiments, the compound is a compound of Formula II, IIa, IIb, IIc, or IId wherein R¹ is selected from the group consisting of hydrogen, halogen, CH₃, OCH₃, CF₃, and OCF₃. In some embodiments, R¹ is hydrogen. In other embodiments, R¹ is halogen.

In some embodiments, the compound is a compound of Formula II, IIa, IIb, IIc, or IId wherein R³, R⁴, R⁵, and R⁶ are each independently selected from the group consisting of hydrogen, halogen, OH, CH₃, OCH₃, CF₃, and OCF₃. For example, in some embodiments, R³, R⁴, R⁵, and R⁶ are each hydrogen.

In some embodiments, the compound is a compound of Formula II, IIa, or IIc wherein X is selected from the group consisting of a bond and O. For example, in some embodiments, X is a bond. In other embodiments, X is O.

In some embodiments, the compound is a compound of Formula II, IIa, or IIb wherein Y is a carboxylic acid isostere selected from the group consisting of tetrazolyl, aminosulfonyl, acylaminosulfonyl, methylsulfonylcarbamyl, thiazolidinedionyl, oxazolidinedionyl, oxadiazolonyl, P(O)(OH)₂, P(O)(OH)H, and SO₃H.

In some embodiments, the compound is a compound of Formula II, IIc, or IId wherein Y is a prodrug of carboxylic acid selected from the group consisting of CH₂OH and an ester group C(O)OR¹¹; wherein R¹¹ is selected from the group consisting of methyl, ethyl, 2-oxopropyl, 2-morpholinoethyl and pivaloyloxymethyl. For example, in some embodiments, Y is C(O)OCH₃. In other embodiments, Y is CH₂OH. In still further embodiments, Y is methoxy.

In another embodiment, the compound is a compound of Formula III or a salt thereof,

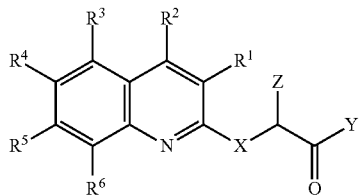

Formula III

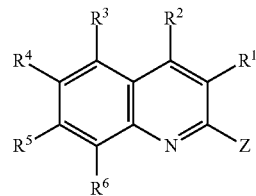

Formula IV wherein $R^1$ is selected from the group consisting of hydrogen, halogen, alkyl, alkoxy, haloalkyl, and haloalkoxy;

$R^2$ is selected from the group consisting of aryl and heteroaryl, each of which may be optionally independently substituted with one or more substituents selected from the group consisting of halogen, OH, CN, alkyl, alkoxy, haloalkyl, haloalkoxy, alkenyl, $C_1$ to $C_4$ hydroxyalkyl, $N(R^7R^8)$, and $NR^9C(O)R^{10}$, wherein $R^7$ and $R^8$ are each independently selected from the group consisting of hydrogen and alkyl, and wherein $R^9$ is selected from the group consisting of hydrogen and alkyl and $R^{10}$ is alkyl;

$R^3$, $R^4$, $R^5$, and $R^6$ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl;

X is selected from the group consisting of $CH_2$, O, S, NH, and $N(CH_3)$;

Y is selected from the group consisting of OH, $NH_2$, $N(H)OH$, $N(CH_3)OH$, and $N(R^7R^8)$, wherein $R^7$ and $R^8$ are each independently selected from the group consisting of hydrogen, alkyl, and hydroxyalkyl; and Z is selected from the group consisting of hydrogen, alkyl, haloalkyl, and cycloalkyl.

In some embodiments, $R^2$ is selected from the group consisting of aryl and heteroaryl, each of which may be optionally independently substituted with one or more substituents selected from the group consisting of halogen, OH, $CH_3$, $OCH_3$, $CF_3$, $OCF_3$, and CN. For example, in some embodiments, $R^2$ is phenyl.

In some embodiments, the compound is a compound of Formula III wherein $R^1$ is selected from the group consisting of hydrogen, halogen, $CH_3$, $OCH_3$, $CF_3$, and $OCF_3$. In some embodiments, $R^1$ is hydrogen. In other embodiments, $R^1$ is halogen.

In some embodiments, the compound is a compound of Formula III wherein $R^3$, $R^4$, $R^5$, and $R^6$ are each independently selected from the group consisting of hydrogen, halogen, OH, $CH_3$, $OCH_3$, $CF_3$, and $OCF_3$. In some embodiments, $R^3$, $R^4$, $R^5$, and $R^6$ are each hydrogen.

In some embodiments, the compound is a compound of Formula III wherein X is S.

In some embodiments, the compound is a compound of Formula III wherein Y is selected from the group consisting of OH and $NH_2$. For example, in some embodiments, Y is OH. In other embodiments, Y is $NH_2$.

In some embodiments, the compound is a compound of Formula III wherein Z is alkyl. For example, in some embodiments, Z is $CH_3$.

In another embodiment, the compound is a compound of Formula IV or a salt thereof, wherein $R^1$ is selected from the group consisting of hydrogen, halogen, alkyl, alkoxy, haloalkyl, and haloalkoxy;

$R^2$ is selected from the group consisting of aryl and heteroaryl, each of which may be optionally independently substituted with one or more substituents selected from the group consisting of halogen, OH, CN, alkyl, alkoxy, haloalkyl, haloalkoxy, alkenyl, $C_1$ to $C_4$ hydroxyalkyl, $N(R^7R^8)$, and $NR^9C(O)R^{10}$, wherein $R^7$ and $R^8$ are each independently selected from the group consisting of hydrogen and alkyl, and wherein $R^9$ is selected from the group consisting of hydrogen and alkyl and $R^{10}$ is alkyl;

$R^3$, $R^4$, $R^5$, and $R^6$ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl; and Z is selected from the group consisting of aryl and heteroaryl, each of which may be optionally independently substituted with one or more substituents selected from the group consisting of halogen, alkyl, alkoxy, haloalkyl, and haloalkoxy, $C_1$ to $C_4$ hydroxyalkyl, CN, and C(H)O.

In some embodiments, $R^2$ is selected from the group consisting of aryl and heteroaryl, each of which may be optionally independently substituted with one or more substituents selected from the group consisting of halogen, OH, $CH_3$, $OCH_3$, $CF_3$, $OCF_3$, and CN. For example, in some embodiments, $R^2$ is phenyl.

In some embodiments, Z is selected from the group consisting of aryl and heteroaryl, each of which may be optionally independently substituted with one or more substituents selected from the group consisting of halogen, $CH_3$, $OCH_3$, $CF_3$, $OCF_3$, CN, and C(H)O.

For example, in some embodiments, Z is selected from the group consisting of phenyl and thienyl. In some embodiments, Z is phenyl. In other embodiments, Z is thienyl.

As used herein, the term "halo" or "halogen" refers to any radical of fluorine, chlorine, bromine or iodine.

The term "alkyl" as employed herein, by itself or as part of another group, refers to both straight and branched chain radicals of up to ten carbons. Non-limiting examples of $C_1$-$C_{10}$ alkyl groups include methyl, ethyl, propyl, isopropyl, butyl, sec-butyl, tert-butyl, 3-pentyl, hexyl and octyl groups. For example, in some embodiments, the term "alkyl" as used herein, by itself or as part of another group, refers to a straight or branched chain radical comprising from one to six carbon atoms.

The term "hydroxyalkyl" as employed herein, refers to both straight and branched chain alkyl radicals having a hydroxyl substituent. The hydroxyl substituent can be bound to any carbon of the alkyl chain. Non-limiting examples include $CH_2OH$, $CH_2CH_2OH$, $CH_2CH(OH)CH_3$ and $CH_2CH(OH)CH_2CH_3$.

The term "haloalkyl" as employed herein, by itself or as part of another group, refers to an alkyl group, as defined herein, substituted with at least one halogen. Non-limiting examples of haloalkyl groups include trifluromethyl and 2,2,2-trifluoroethyl.

The term "alkoxy" as employed herein, by itself or as part of another group, refers to an alkyl group, as defined herein, appended to the parent molecular moiety through an oxygen atom. Non-limiting examples of alkoxy groups include methoxy, ethoxy, propoxy, 2-propoxy, butoxy, tert-butoxy, pentyloxy, and hexyloxy.

The term "haloalkoxy" as employed herein, by itself or as part of another group, refers to an alkoxy group as defined herein, wherein the alkyl moiety of the alkoxy group is further substituted with at least one halogen. Non-limiting example of haloalkoxy groups include trifluoromethoxy, and 2,2-dichloroethoxy.

The term "cycloalkyl" as used herein refers to an alkyl group comprising a closed ring comprising from 3 to 8 carbon atoms. Non-limiting examples of cycloalkyl groups include cyclopropyl, cyclobutyl, cyclopentyl, cyclohexyl and cycloheptyl.

The term "aryl" as employed herein by itself or as part of another group refers to monocyclic, bicyclic or tricyclic aromatic groups containing from 6 to 14 carbons in the ring. Common aryl groups include $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

The term "heteroaryl" as employed herein refers to groups having 5 to 14 ring atoms; 6, 10 or 14 it electrons shared in a cyclic array; and containing carbon atoms and 1, 2 or 3 oxygen, nitrogen or sulfur heteroactoms. Example heteroaryl groups include thienyl (thiophenyl), benzo[b]thienyl, naphtho[2,3-b]thienyl, thianthrenyl, furyl (furanyl), pyranyl, isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-α]pyrimidin-4-one, pyrazolo[1,5-a]pyrimidinyl, including without limitation pyrazolo[1,5-α]pyrimidin-3-yl, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "prodrug of a carboxylic acid" as employed herein refers to any compound or moiety that can be transformed through chemical or metabolic (enzymatic) processes in vivo to produce carboxylic acid. The prodrug of a carboxylic acid may be an inactive or less active compound than the parent compound containing the carboxylic acid. A prodrug of a carboxylic acid may have physicochemical properties which result in improved uptake, distribution or metabolism. In a non-limiting example of a prodrug of a carboxylic acid, carboxylic acid can be esterified with a methyl or ethyl group to yield an ester and when the carboxylic acid ester is administered to a biological system (e.g. plant or human subject) the ester group may be, for example, converted enzymatically, non-enzymatically, oxidatively or hydrolytically to a carboxylate group. Additionally, convertible prodrugs of carboxylic acid moieties include, but are not limited to, substituted and unsubstituted, branched and unbranched lower alkyl ester moieties (methyl ester, ethyl esters, propyl esters, butyl esters, pentyl esters, cyclopentyl esters, hexyl esters and cyclohexyl esters), lower alkenyl esters, acyloxy lower alkyl esters (e.g. pivaloyloxymethyl ester), aryl esters, and aryl lower alkyl esters (e.g. benzyl esters). Alternatively, hydroxyalkyl groups may be oxidized in vivo to a carboxylic acid. Additionally, conventional procedures for selection and preparation of suitable prodrug of a carboxylic acid derivatives are known in the art including, for example, as described in "Prodrugs: Challengs and Rewards," Part 2, Volume 5 (2007) pages 3-29 and "Current Methods in Medicinal Chemistry and Biological Physics" Volume 2 (2008) pages 187-214", which are incorporated herein by reference.

The term "carboxylic acid isostere" as employed herein includes each and all of (1) carboxylic acid isosteres having one or more of the following, the same number of atoms, the same number of valence electrons, and exhibiting similar reactive electron shells, volumes and shapes as compared to a carboxylic acid substituent, and (2) non-classical isosteres which fit the broadest definition of isosters and produce biological effects similar to a carboxylic acid substituent. Non-limiting examples of carboxylic acid isosteres include tetrazolyl, aminosulfonyl, acylaminosulfonyl, methylsulfonylcarbamyl, thiazolidinedionyl, oxazolidinedionyl, oxadiazolonyl, P(O)(OH)$_2$, P(O)(OH)H, and SO$_3$H. The concept of carboxylic acid isostere in drug design and the properties of several isosters are known in the art and described, for example, by Ballatore at al in ChemMedChem 2013, 8, pages 385-395, which is incorporated herein by reference.

Non-limiting examples of species include 2-(4-(4-phenylquinolin-2-yl)phenoxy)acetamide of Formula Ia-i, or a salt thereof, Formula Ia-i

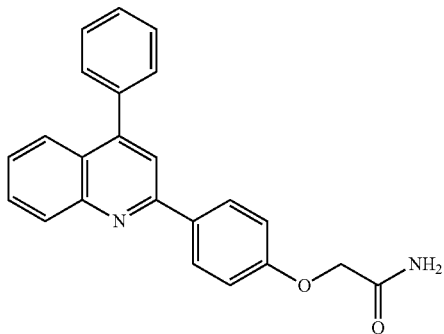 [SMILES: NC(=O)COc1ccc(-c2cc(-c3ccccc3)c3ccccc3n2)cc1]

2-(4-(4-phenylquinolin-2-yl)phenoxy)acetic acid of Formula Ia-ii, or a salt thereof,

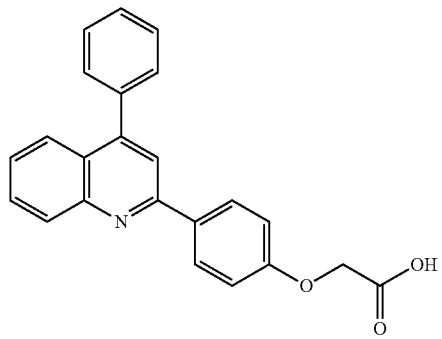

Formula Ia-ii 2-(4-(8-methoxy-4-phenylquinolin-2-yl)phenoxy)acetamide of Formula Ia-iii, or a salt thereof,

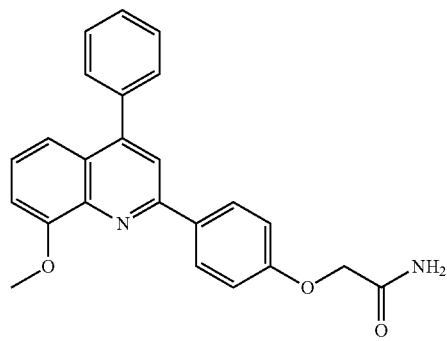

Formula Ia-iii 2-(4-(8-ethyl-4-phenylquinolin-2-yl)phenoxy)acetamide of Formula Ia-iv, or a salt thereof,

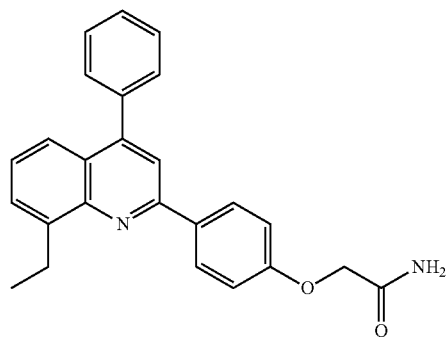

Formula Ia-iv 2-(4-(6-chloro-4-phenylquinolin-2-yl)phenoxy)-N-(2-hydroxyethyl)acetamide of Formula Ia-v, or a salt thereof,

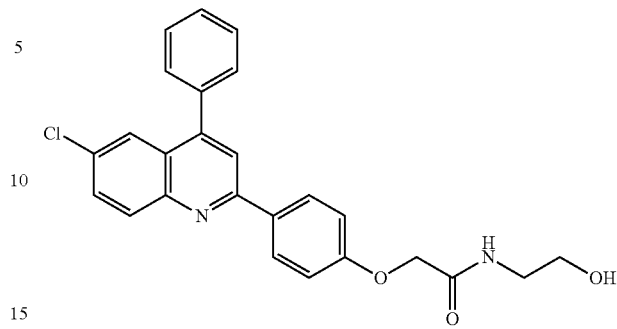

Formula Ia-v 2-(5-(3-chloro-4-phenylquinolin-2-yl)thiophen-2-yl)acetamide of Formula Ib-i, or a salt thereof,

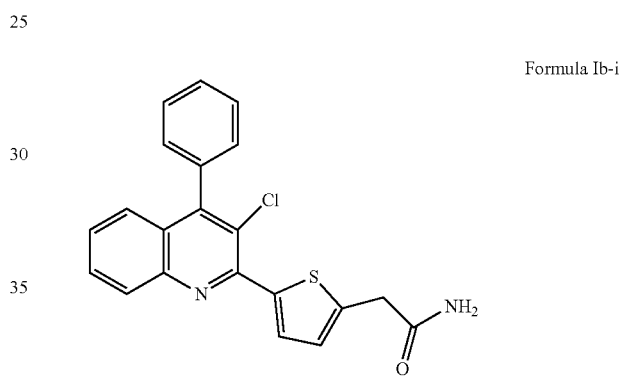

Formula Ib-i 2-(5-(3-chloro-4-phenylquinolin-2-yl)thiophen-2-yl)acetic acid of Formula Ib-ii, or a salt thereof,

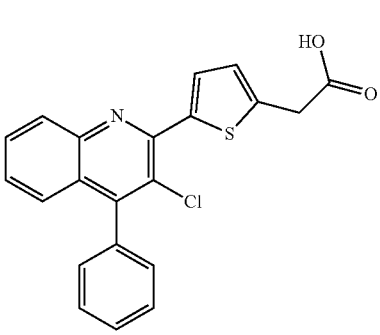

Formula Ib-ii 2-(5-(4-phenylquinolin-2-yl)thiophen-2-yl)acetamide of Formula Ib-iii, or a salt thereof,

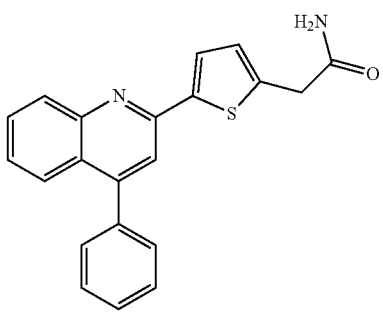

2-(5-(4-phenylquinolin-2-yl)thiophen-2-yl)acetic acid of Formula Ib-iv, or a salt thereof,

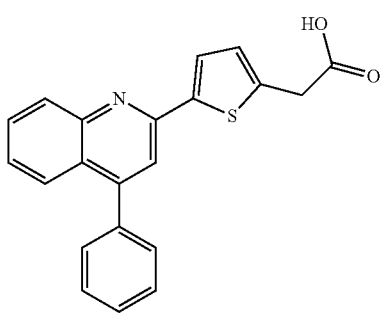

2-(5-(8-methoxy-4-phenylquinolin-2-yl)thiophen-2-yl)acetamide of Formula Ib-v, or a salt thereof,

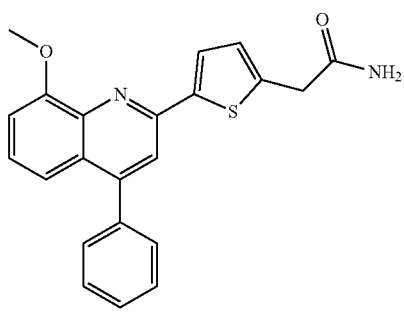

2-(5-(8-ethyl-4-phenylquinolin-2-yl)thiophen-2-yl)acetamide of Formula Ib-vi, or a salt thereof, 2-(4-((1H-tetrazol-5-yl)methoxy)phenyl)-4-phenylquinoline of Formula IIa-i, or a salt thereof,

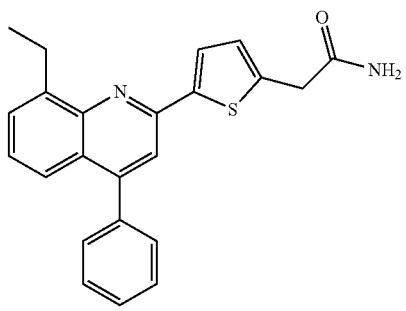

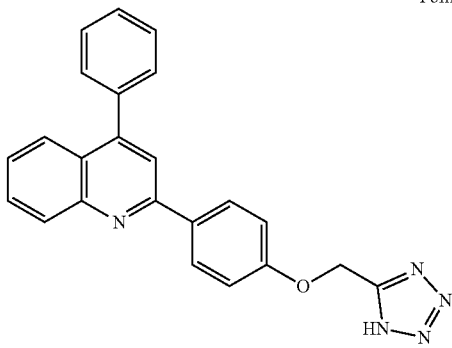

((4-(4-phenylquinolin-2-yl)phenoxy)methyl)phosphonic acid of Formula IIa-ii, or a salt thereof,

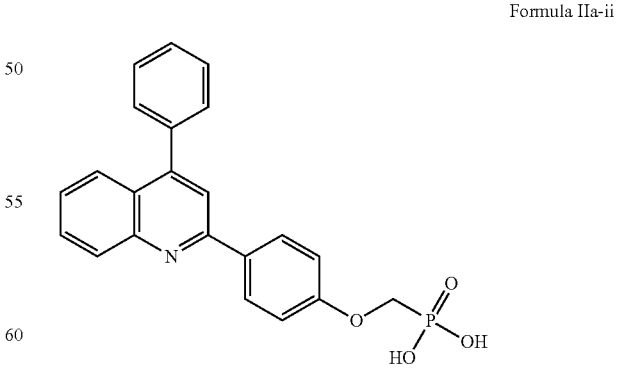

((4-(4-phenylquinolin-2-yl)phenoxy)methyl)phosphinic acid of Formula IIa-iii, or a salt thereof, Formula IIa-iii

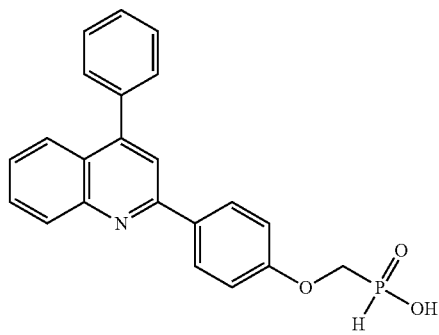

(4-(4-phenylquinolin-2-yl)phenoxy)methanesulfonamide of Formula IIa-iv, or a salt thereof, Formula IIa-iv

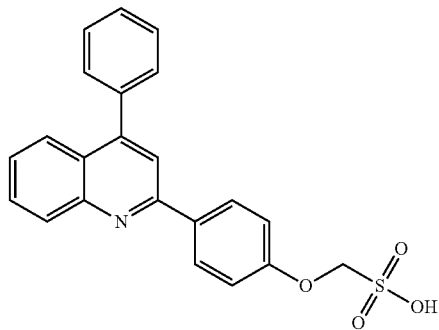

(4-(4-phenylquinolin-2-yl)phenoxy)methanesulfonamide of Formula IIa-v, or a salt thereof, Formula IIa-v

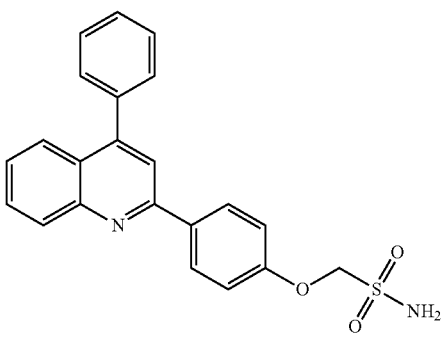

N-(methylsulfonyl)-2-(4-(4-phenylquinolin-2-yl)phenoxy) acetamide of Formula IIa-vi, or a salt thereof, Formula IIa-vi

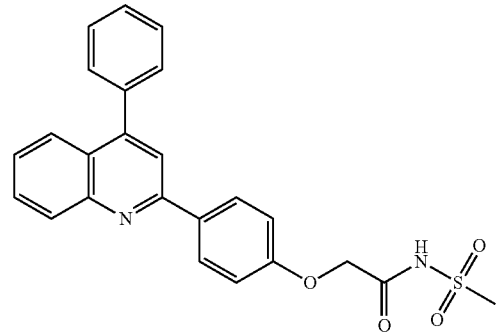

5-((4-(4-phenylquinolin-2-yl)phenoxy)methyl)thiazolidine-2,4-dione of Formula IIa-vii, or a salt thereof, Formula IIa-vii 5-((4-(4-phenylquinolin-2-yl)phenoxy)methyl)oxazolidine-2,4-dione of Formula IIa-viii, or a salt thereof, Formula IIa-viii

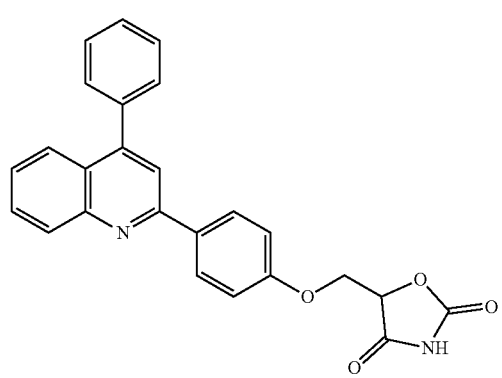

3-((4-(4-phenylquinolin-2-yl)phenoxy)methyl)-1,2,4-oxadiazol-5(4H)-one of Formula IIa-ix, or a salt thereof,

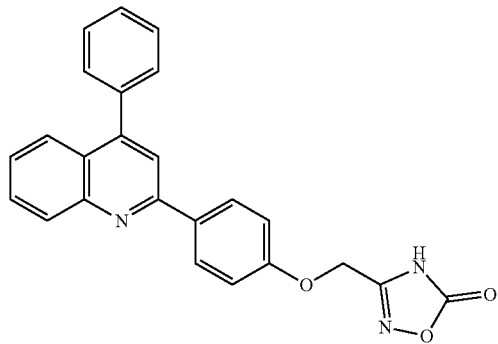

2-(5-((1H-tetrazol-5-yl)methyl)thiophen-2-yl)-4-phenylquinoline of Formula IIb-i, or a salt thereof,

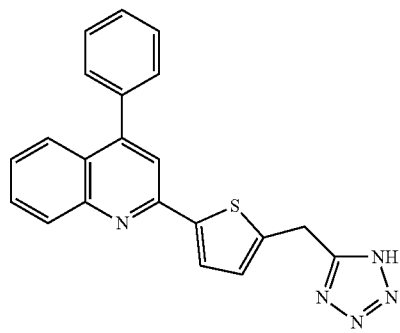

((5-(4-phenylquinolin-2-yl)thiophen-2-yl)methyl)phosphonic acid of Formula IIb-ii, or a salt thereof,

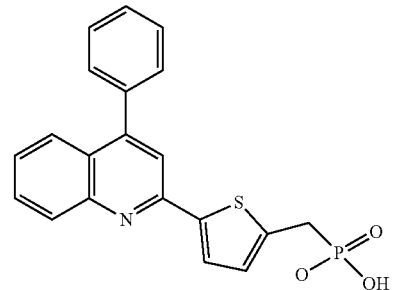

((5-(4-phenylquinolin-2-yl)thiophen-2-yl)methyl)phosphonic acid of Formula IIb-iii, or a salt thereof,

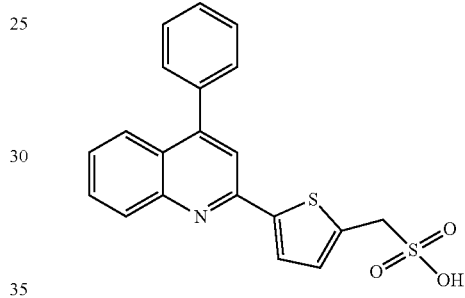

(5-(4-phenylquinolin-2-yl)thiophen-2-yl)methanesulfonic acid of Formula IIb-iv, or a salt thereof, (5-(4-phenylquinolin-2-yl)thiophen-2-yl)methanesulfonamide of Formula IIb-v, or a salt thereof,

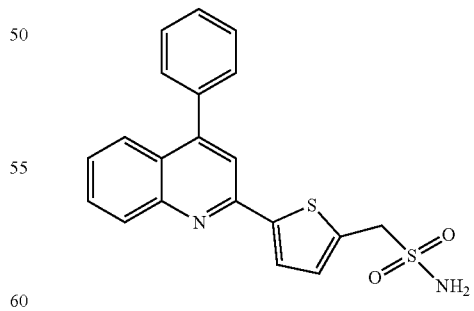

N-(methylsulfonyl)-2-(5-(4-phenylquinolin-2-yl)thiophen-2-yl)acetamide of Formula IIb-vi, or a salt thereof, Formula IIb-vi

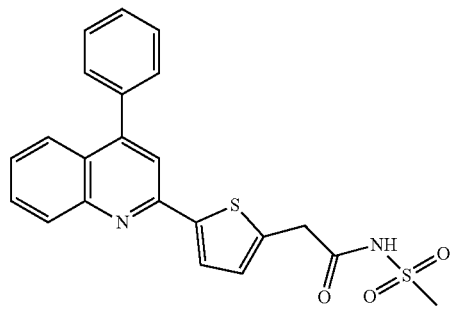

5-((5-(4-phenylquinolin-2-yl)thiophen-2-yl)methyl)thiazo-lidine-2,4-dione of Formula IIb-vii, or a salt thereof, Formula IIb-vii

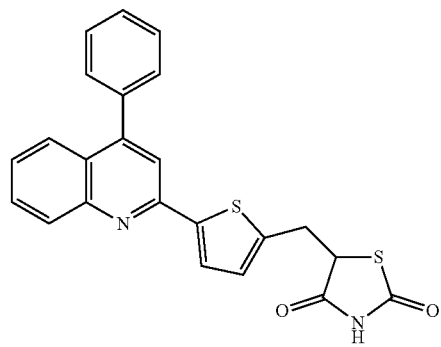

5-((5-(4-phenylquinolin-2-yl)thiophen-2-yl)methyl)oxazoli-dine-2,4-dione of Formula IIb-viii, or a salt thereof, Formula IIb-viii

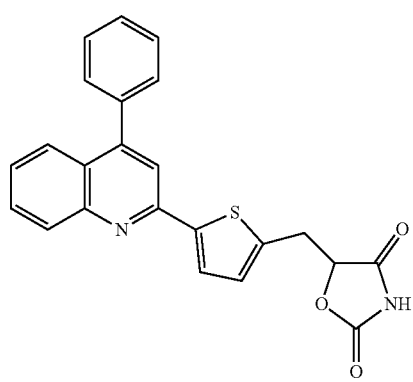

3-((5-(4-phenylquinolin-2-yl)thiophen-2-yl)methyl)-1,2,4-oxadiazolidin-5-one of Formula IIb-ix, or a salt thereof, Formula IIb-ix

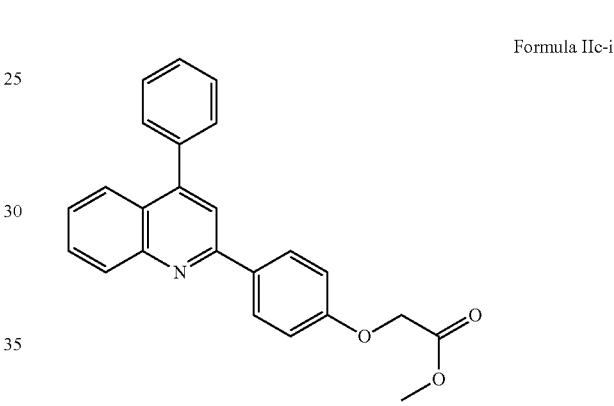

methyl 2-(4-(4-phenylquinolin-2-yl)phenoxy)acetate of Formula IIc-i, or a salt thereof, Formula IIc-i methyl 2-(5-(4-phenylquinolin-2-yl)thiophen-2-yl)acetate of Formula IId-i, or a salt thereof, Formula IId-i

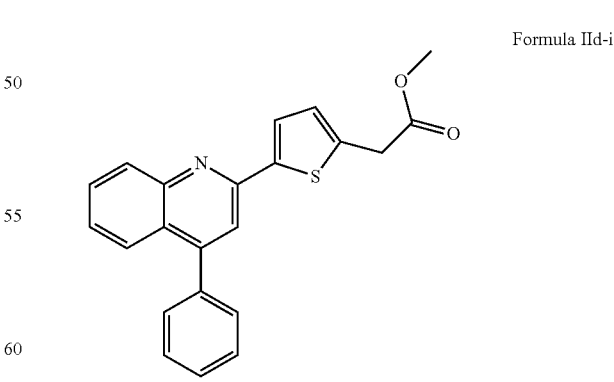

methyl 2-(5-(3-chloro-4-phenylquinolin-2-yl)thiophen-2-yl)acetate of Formula IId-ii, or a salt thereof,

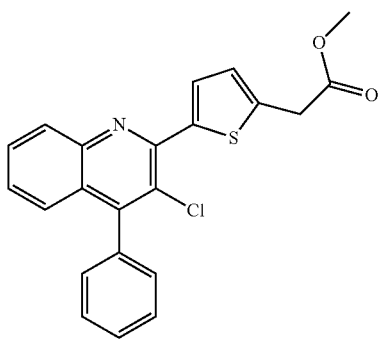

2-((7-methoxy-4-phenylquinolin-2-yl)thio)propanamide of Formula III-i, or a salt thereof,

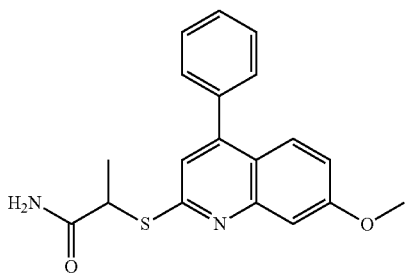

2-(4-methoxyphenyl)-4-phenylquinoline of Formula IV-i, or a salt thereof, and

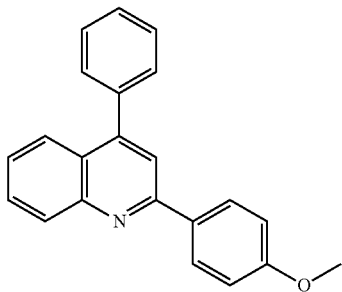

2-(3,4-dimethoxyphenyl)-4-phenylquinoline of Formula IV-ii, or a salt thereof.

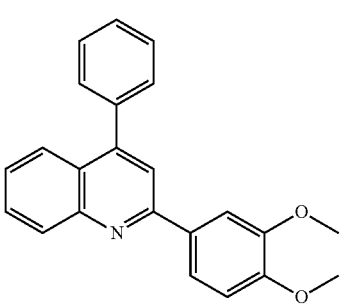

Enantiomers

The compounds described herein may be present as a racemic mixture, as a mixture of two enantiomers at different ratios, or as a single enantiomer. Compositions that are enriched with respect to one enantiomer, or which comprise substantially a single enantionmer, may be prepared using any technique known in the art, including chiral separation techniques known in the art (e.g., chiral chromatography or asymmetric synthesis).

Compositions

In another aspect, the present disclosure is generally related to a composition comprising an effective amount of a compound (e.g., a compound of Formula I, Ia, Ib, II, IIa, IIb, IIc, IId, III, or IV) as described herein as an ACCase modulator or inhibitor for use in administration to a plant, a seed, or soil to control fungal pathogens.

For example, the composition may be an aqueous composition.

Generally, the compositions described herein can comprise any adjuvants, excipients, or other desirable components known in the art.

Non-limiting examples of additional ingredients include surfactants, co-surfactants, permeation enhancers, and co-solvents. For example, the composition may comprise as SPAN surfactants, TWEEN surfactants, TRITON surfactants, MAKON surfactants, IGEPAL surfactants, BRIJ surfactants, MORWET surfactants, PLURONIC surfactants, LANEXOL surfactants, ATLOX surfactants, ATLAS surfactants, SURFYNOL surfactants, TERGITOL surfactants, DOWFAX surfactants, TOXIMUL surfactants, SILWET surfactants, SYLGARD surfactants, BREAK THRU surfactants, PHYTOSAN, SOLUPLUS, cyclodextrans, polypropylene glycol, ethyl lactate, methyl soyate/ethyl lactate co-solvent blends (e.g., STEPOSOL), isopropanol, acetone, ethylene glycol, propylene glycol, n-alkylpyrrolidones (e.g., the AGSOLEX series), a petroleum based-oil (e.g., AROMATIC 200) or a mineral oil (e.g., paraffin oil)).

For example, in some embodiments, the composition comprises a surfactant. Non-limiting examples of surfactants include SPAN 20, SPAN 40, SPAN 80, SPAN 85, TWEEN 20, TWEEN 40, TWEEN 80, TWEEN 85, TRITON X 100, MAKON 10, IGEPAL CO 630, BRIJ 35, BRIJ 97, TERGITOL TMN 6, DOWFAX 3B2, PHYSAN and TOXIMUL TA 15.

In some embodiments, the composition comprises a co-solvent. Examples of co-solvents that can be used include ethyl lactate, methyl soyate/ethyl lactate co-solvent blends (e.g., STEPOSOL), isopropanol, acetone, 1,2-propanediol, n-alkylpyrrolidones (e.g., the AGSOLEX series), a petroleum based-oil (e.g., AROMATIC 200) or a mineral oil (e.g., paraffin oil)).

In some embodiments, the composition may be formulated, mixed in a tank, combined on a seed by overcoating, or recommended for use with one or more additional active ingredients on a seed, plant, or soil. The additional active ingredient may be, for example, an additional pesticide. The pesticide may be, for example, an insecticide, a fungicide, an herbicide, or an additional nematicide.

Non-limiting examples of insecticides and nematicides include carbamates, diamides, macrocyclic lactones, neonicotinoids, organophosphates, phenylpyrazoles, pyrethrins, spinosyns, synthetic pyrethroids, tetronic and tetramic acids. In another embodiment, insecticides and nematicides include abamectin, aldicarb, aldoxycarb, bifenthrin, carbofuran, chlorantraniliprole, clothianidin, cyfluthrin, cyhalothrin, cypermethrin, deltamethrin, dinotefuran, emamectin, ethiprole, fenamiphos, fipronil, flubendiamide, fosthiazate, imidacloprid, ivermectin, lambda-cyhalothrin, milbemectin, nitenpyram, oxamyl, permethrin, spinetoram, spinosad, spirodichlofen, spirotetramat, tefluthrin, thiacloprid, thiamethoxam, and thiodicarb.

In some embodiments, the composition comprises an insecticide and/or acaricide that inhibits ACCase activity. Non-limiting examples include tetramic acids such as spirotetramat, and tetronic acids including spiromesifen and spirodiclofen.

In some embodiments, the composition comprises one or more nematicidal compounds as described in U.S. Pub. Nos. 2009/0048311 A1 or 2011/028320 A1, or WO 2012/030887 A1, the contents of which are herein incorporated by reference.

For example, in some embodiments, the composition comprises 3-phenyl-5 (thiophen-2-yl)-1,2,4-oxadiazole.

Non-limiting examples of herbicides include ACCase inhibitors, acetanilides, AHAS modulators or inhibitors, carotenoid biosynthesis inhibitors, EPSPS modulators or inhibitors, glutamine synthetase modulators or inhibitors, PPO modulators or inhibitors, PS II modulators or inhibitors, and synthetic auxins. Non-limiting examples of herbicides include acetochlor, clethodim, dicamba, flumioxazin, fomesafen, glyphosate, glufosinate, mesotrione, quizalofop, saflufenacil, sulcotrione, and 2,4-D.

In one embodiment, an herbicide compound is selected that inhibits ACCase activity. Non-limiting examples include herbicidal aryloxyphenoxypropionates such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, kuicaoxi, metamifop, propaquizafop, quizalofop, quizalofop-P, and trifop, herbicidal cyclohexanediones such as alloxydim, butroxydim, clethodim, cloproxydim, cycloxydim, profoxydim, sethoxydim, tepraloxydim, and tralkoxydim, as well as the herbicide pinoxaden.

The herbicides cycloxydim and sethoxydim are known to exhibit moderate antifungal activity alone, and, without being bound to a particular theory, it is believed that the combination of these species with the compounds described herein may enhance fungal control by the additional suppression of ACCase.

The composition may comprise one or more additional fungicides. Non-limiting examples of additional fungicides include aromatic hydrocarbons, benzimidazoles, benzothiadiazole, carboxamides, carboxylic acid amides, morpholines, phenylamides, phosphonates, quinine outside inhibitors (e.g. strobilurins), thiazolidines, thiophanates, thiophene carboxamides, and triazoles, Particular examples of fungicides include acibenzolar-S-methyl, azoxystrobin, benalaxyl, bixafen, boscalid, carbendazim, cyproconazole, dimethomorph, epoxiconazole, fluopyram, fluoxastrobin, flutianil, flutolanil, fluxapyroxad, fosetyl-Al, ipconazole, isopyrazam, kresoxim-methyl, mefenoxam, metalaxyl, metconazole, myclobutanil, orysastrobin, penflufen, penthiopyrad, picoxystrobin, propiconazole, prothioconazole, pyraclostrobin, sedaxane, silthiofam, tebuconazole, thifluzamide, thiophanate, tolclofos-methyl, trifloxystrobin, and triticonazole.

In some embodiments, the composition comprises one or more additional fungicides that modulate or inhibit ACCase activity.

The composition may also comprise one or more additional active substances, including biological control agents, microbial extracts, natural products, plant growth activators and/or plant defense agents. Non-limiting examples of biological control agents include bacteria, fungi, beneficial nematodes, and viruses.

For example, in certain embodiments, the biological control agent can be a bacterium of the genus *Actinomycetes, Agrobacterium, Arthrobacter, Alcaligenes, Aureobacterium, Azobacter, Beijerinckia, Brevibacillus, Burkholderia, Chromobacterium, Clostridium, Clavibacter, Comamonas, Corynebacterium, Curtobacterium, Enterobacter, Flavobacterium, Gluconobacter, Hydrogenophage, Klebsiella, Methylobacterium, Paenibacillus, Pasteuria, Photorhabdus, Phyllobacterium, Pseudomonas, Rhizobium, Serratia, Sphingobacterium, Stenotrophomonas, Variovax,* and *Xenorhabdus.*

In some embodiments, the biological control agent can be a fungus of the genus *Alternaria, Ampelomyces, Aspergillus, Aureobasidium, Beauveria, Colletotrichum, Coniothyrium, Gliocladium, Metarhizium, Muscodor, Paecilomyces, Trichoderma, Typhula, Ulocladium,* and *Verticillium.* In particular embodiments the fungus is *Beauveria bassiana, Coniothyrium minitans, Gliocladium virens, Muscodor albus, Paecilomyces lilacinus,* or *Trichoderma polysporum.*

In further embodiments, the biological control agents can be plant growth activators or plant defense agents including, but not limited to harpin, *Reynoutria sachalinensis,* jasmonate, lipochitooligosaccharides, and isoflavones.

Methods of Use

ACCase is an essential catalyst for the rate-limiting step of fatty acid biosynthesis in both eukaryotes and prokaryotes. Without being bound to a particular theory, it is believed that the compounds disclosed herein modulate or inhibit ACCase. In one embodiment, a compound (e.g., a compound of Formula I, Ia, Ib, II, IIa, IIb, IIc, IId, III, or IV) as described herein is used as a ACCase modulator. Additionally, compounds as described herein of Formulas I, Ia, Ib, II, IIa, IIb, IIc, IId, III, or IV are also believed to exhibit control of phytopathogenic fungi, as described herein. In one embodiment, the compounds disclosed herein are administered to a plant, a seed, or soil in a composition as described herein to control fungal pathogens, including using the compounds as described herein with any adjuvants, excipients, or other desirable components as described herein or known in the art and formulating, mixing, or combining one or more additional active ingredients. The additional active ingredient may be, for example, an additional pesticide. The pesticide may be, for example, an insecticide, a fungicide, an herbicide, or an additional nematicide as described herein or otherwise known in the art.

The compounds and compositions described herein can be administered to seeds, plants, or the environment of plants (e.g., soil) wherein the control of phytopathogenic fungi is desired. For example, in one embodiment, the disclosure is generally related to a method of controlling fungal pathogens, the method comprising administering to a plant, a seed or soil a composition comprising an effective amount of a compound as described herein.

Non-limiting examples of plants that may be protected from fungal pathogens in accordance with the methods described herein include monocotyledon crops such as corn, wheat, barley, rye, rice, sorghum, oat; sugarcane and turf; and dicotyledon crops such as cotton, sugar beet, peanut, potato, sweet potato, yam, sunflower, soybean, alfalfa, canola, grapes, tobacco; vegetables including Solanaceae vegetables such as eggplant, tomato, green pepper and pepper; Cucurbitaceae vegetables such as cucumber, pumpkin, zucchini, watermelon, melon and squash; Brassicaceae vegetables such as radish, turnip, horseradish, Chinese cabbage, cabbage, leaf mustard, broccoli and cauliflower; Asteraceae vegetables such as artichoke and lettuce; Liliaceae vegetables such as leek, onion, garlic and asparagus; Apiaceae vegetables such as carrot, parsley, celery and parsnip; Chenopodiaceae vegetables such as spinach and chard; Lamiaceae vegetables such as mint and basil; flowers such as *petunia*, morning glory, carnation, *chrysanthemum* and rose; foliage plants; fruit trees such as pome fruits (e.g., apple, pear and Japanese pear), stone fruits (e.g., peach, plum, nectarine, cherry, apricot and prune), citrus (e.g., orange, lemon, lime and grapefruit), tree nuts (e.g., chestnut, pecan, walnut, hazel, almond, pistachio, cashew and macadamia), berries such as blueberry, cranberry, blackberry, strawberry and raspberry; persimmon; olive; loquat; banana; coffee; palm; coco; the other trees such tea, mulberry, flower trees, and landscape trees (e.g., ash, birch, dogwood, *eucalyptus*, ginkgo, lilac, maple, oak, poplar, *Formosa* sweet gum, sycamore, fir, hemlock fir, needle juniper, pine, spruce, yew).

Non-limiting examples of the plant diseases that may be controlled by the methods described herein include diseases caused by phytopathogenic fungi (in particular of the classes of Ascomycetes, Deuteromycetes, Oomycetes and Basidiomycetes) such as *Magnaporthe grisea, Cochliobolus miyabeanus, Rhizoctonia solani* and *Gibberella fujikuroi* on rice; *Erysiphe graminis, Fusarium graminearum, F. avenacerum, F. culmorum, Microdochium nivale, Puccinia striiformis, P. graminis, P. recondita, P. hordei, Typhula* sp., *Micronectriella nivalis, Ustilago tritici, U. nuda, Tilletia caries, Pseudocercosporella herpotrichoides, Rhynchosporium secalis, Septoria tritici, Leptosphaeria nodorum* and *Pyrenophora teres* on wheat and barley; *Diaporthe citri, Elsinoe fawcetti, Penicillium digitatum, P. italicum, Phytophthora parasitica* and *Phytophthora citrophthora* on citrus; *Monilinia mali, Valsa ceratosperma, Podosphaera leucotricha, Alternaria alternata* apple pathotype, *Venturia inaequalis, Colletotrichum acutatum* and *Phytophtora cactorum* on apple; *Venturia nashicola, V. pirina, Alternaria alternata* Japanese pear pathotype, *Gymnosporangium haraeanum* and *Phytophthora cactorum* on pear; *Monilinia fructicola, Cladosporium carpophilum* and *Phomopsis* sp. on peach; *Elsinoe ampelina, Glomerella cingulata, Uncinula necator, Phakopsora ampelopsidis, Guignardia bidwellii* and *Plasmopara viticola* on grape; *Gloeosporium kaki, Cercospora kaki* and *Mycosphaerella nawae* on persimmon; *Colletotrichum lagenarium, Sphaerotheca fuliginea, Mycosphaerella melonis, Fusarium oxysporum, Pseudoperonospora cubensis* and *Phytophthora* sp. on *Cucurbitales* vegetables; *Alternaria solani, Cladosporium fulvum* and *Phytophthora infestans* on tomato; *Phomopsis vexans* and *Erysiphe cichoracearum* on eggplant; *Alternaria japonica, Cercosporella brassicae, Plasmodiophora brassicae* and *Peronospora parasitica* on Brassicaceae vegetables; *Puccinia allii* and *Peronospora destructor* on leek; *Cercospora kikuchii, Elsinoe glycines, Diaporthe phaseolorum* var. *sojae, Phakopsora pachyrhizi* and *Phytophthora sojae* on soybean; *Colletotrichum lindemuthianum* of kidney bean; *Cercospora personata, Cercospora arachidicola* and *Sclerotium rolfsii* on peanut; *Erysiphe pisi* on pea; *Alternaria solani, Phytophthora infestans, Phytophthora erythroseptica* and *Spongospora subterranean* f sp. *subterranean* on potato; *Sphaerotheca humuli* and *Glomerella cingulata* on strawberry; *Exobasidium reticulatum, Elsinoe leucospila, Pestalotiopsis* sp. and *Colletotrichum theae-sinensis* on tea; *Alternaria longipes, Erysiphe cichoracearum, Colletotrichum tabacum, Peronospora tabacina* and *Phytophthora nicotianae* on tobacco; *Cercospora beticola, Thanatephorus cucumeris*, and *Aphanidermatum cochlioides* on sugar beet; *Diplocarpon rosae, Sphaerotheca pannosa* and *Peronospora sparsa* on rose; *Bremia lactucae, Septoria chrysanthemi-*indici and *Puccinia horiana* on chrysanthemum and Compositae vegetables; *Alternaria brassicicola* on radish; *Sclerotinia homeocarpa* and *Rhizoctonia solani* on turf; *Mycosphaerella fijiensis* and *Mycosphaerella musicola* on banana; *Plasmopara halstedii* on sunflower; and various diseases on crops caused by *Aspergillus* spp., *Alternaria* spp., *Cephalosporium* spp., *Cercospora* spp., *Cochliobolus* spp., *Diaporthe* spp., *Phomopsis* spp., *Diplodia* spp., *Fusarium* spp., *Gibberella* spp., *Helminthosporium* spp., *Phakopsora* spp., *Phytophthora* spp., *Blumeria* spp., *Oidium* spp., *Erysiphe* spp., *Uncinula* spp., *Podosphaera* spp., *Microsphaera* spp., *Colletotrichum* spp., *Corynespora* spp., *Peronospora* spp., *Plasmopara* spp., *Pythium* spp., *Pyrenophora* spp., *Pythium* spp., *Rhizoctonia* spp., *Rhynchosporium* spp., Botryotinia spp., *Botrytis* spp., *Botryosphaeria* spp., *Sphaerotheca* spp., *Septoria* spp., *Thielaviopsis* spp., Typhula spp., *Pseudocercosporella* spp., *Cochliobolus* spp., Gaeumannomyces spp., *Mucor* spp., *Puccinia* spp., *Tilletia* spp., *Ustilago* spp., *Venturia* spp., *Gymnosporangium* spp., *Claviceps* spp., *Cladosporium* spp., *Physalospora* spp., *Pyricularia* spp., *Magnaporthe* spp., *Rhizopus* spp., *Monilinia* spp., *Cladosporium* spp., *Curvularia* spp., *Sclerotinia* spp., *Sclerotium* sp., *Corticum* spp., *Corticium* spp., *Phoma* spp., *Polymyxa* spp., and *Olpidium* spp.

Application to Plants and/or Soil

Generally, the methods described herein can be used to modulate, inhibit or eradicate fungal pathogens as described herein that cause disease on various parts of agricultural crop plants (e.g., fruit, blossoms, leaves, stems, tubers, roots) or other useful plants as described herein. For example, the methods described herein may be used to modulate, inhibit, and/or control any of the fungal pathogens and/or plant diseases listed above.

For example, the methods described herein may be used to modulate, inhibit or eradicate plant fungal pathogens in vegetable crops, row crops, trees, nuts, vines, turf, and ornamental plants.

In some embodiments, a composition comprising a compound as described herein may be supplied to a plant exogenously. The composition may be applied to the plant and/or the surrounding soil through sprays, drips, and/or other forms of liquid application.

The compounds described herein may penetrate the plant through the roots via the soil (systemic action); by drenching the locus of the plant with a liquid composition; or by applying the compounds in solid form to the soil, e.g. in granular form (soil application).

As used herein, the term "locus" broadly encompasses the fields on which the treated plants are growing, or where the seeds of cultivated plants are sown, or the place where the seed will be placed into the soil.

For example, in some embodiments, a composition is applied to a plant, including plant leaves, shoots, roots or seeds. In one embodiment, a composition comprising a compound as described herein applied to a foliar surface of a plant. Foliar applications may require 50 to 500 g per hectare of a compound as described herein.

As used herein, the term "foliar surface" broadly refers to any green portion of a plant having surface that may permit absorption of silicon, including petioles, stipules, stems, bracts, flowerbuds, and leaves. Absorption commonly occurs at the site of application on a foliar surface, but in some cases, the applied composition may run down to other areas and be absorbed there.

The compositions described herein can be applied to the foliar surfaces of the plant using any conventional system for applying liquids to a foliar surface. For example, in some embodiments, application by spraying will be found most convenient. Any conventional atomization method can be used to generate spray droplets, including hydraulic nozzles and rotating disk atomizers. In some embodiments, alternative application techniques, including application by brush or by rope-wick, may be utilized.

In some embodiments, a composition comprising a compound as described herein is directly applied to the soil surrounding the root zone of a plant. Soil applications may require 0.1 to 5 kg per hectare of a compound as described herein on a broadcast basis (rate per treated area if broadcast or banded).

For example, in some embodiments, a composition may be applied directly to the base of the plants or to the soil immediately adjacent to the plants.

In some embodiments, a sufficient quantity of the composition is applied such that it drains through the soil to the root area of the plants.

Generally, application of the composition may be performed using any method or apparatus known in the art, including but not limited to hand sprayer, mechanical sprinkler, or irrigation, including drip irrigation.

In some embodiments, the composition is applied to plants and/or soil using a drip irrigation technique. For example, the composition may be applied through existing drip irrigation systems. This procedure is used in some embodiments in connection with cotton, strawberries, tomatoes, potatoes, vegetables, and ornamental plants.

In other embodiments, a composition is applied to plants and/or soil using a drench application. The drench application technique is used in some embodiments in connection with crop plants and turf grasses.

In some embodiments, a composition is applied to soil after planting. In other embodiments, however, the composition may be applied to soil during planting, or a treatment composition may be applied to soil before planting.

For example, in some embodiments, a composition may be tilled into the soil or applied in furrow.

In crops of water, such as rice, solid granulates comprising the compounds described herein may be applied to the flooded field or locus of the crop plants to be treated.

Application to Seeds

One embodiment of the disclosure is generally related to a method of protecting a seed, and/or the roots of a plant grown from the seed, against damage by phytopathogenic fungi. The seed treatment methods described herein may be used to modulate, inhibit, and/or control any of the fungal pathogens and/or plant diseases described above. In one embodiment, the method comprises treating a seed with a composition comprising a compound as described herein. As used herein, the term "seed" broadly encompasses plant propagating material such as, tubers cuttings, seedlings, seeds, and germinated or soaked seeds.

In one embodiment, the disclosure relates to a method of administering to a seed a compound (e.g., a compound of Formula I, Ia, Ib, II, IIa, IIb, IIc, IId, III, or IV) as described to control fungal pathogens in a composition as described herein, including using the compounds as described herein with the any adjuvants, excipients, or other desirable components as described herein or known in the art and formulating, mixing, or combining one or more additional active ingredients. The additional active ingredient may be, for example, an additional pesticide. The pesticide may be, for example, an insecticide, a fungicide, an herbicide, or an additional nematicide as described herein or otherwise known in the art.

For example, a compound as described herein may be applied to seeds or tubers by impregnating them with a liquid seed treatment composition comprising a compound described herein, or by coating them with a solid or liquid composition comprising a compound described herein.

Seed treatment methods described herein can be used in connection with any species of plant and/or the seeds thereof as described herein. In some embodiments, however, the methods are used in connection with seeds of plant species that are agronomically important. In particular, the seeds can be of corn, peanut, canola/rapeseed, soybean, cucurbits, crucifers, cotton, beets, rice, sorghum, sugar beet, wheat, barley, rye, sunflower, tomato, sugarcane, tobacco, oats, as well as other vegetable and leaf crops. In some embodiments, the seed is corn, soybean, or cotton seed. The seed may be a transgenic seed from which a transgenic plant can grow and incorporate a transgenic event that confers, for example, tolerance to a particular herbicide or combination of herbicides, insect resistance, increased disease resistance, enhanced tolerance to stress and/or enhanced yield. Transgenic seeds include, but are not limited to, seeds of corn, soybean and cotton.

A seed treatment method may comprise applying a composition to the seed prior to sowing the seed, so that the sowing operation is simplified. In this manner, seeds can be treated, for example, at a central location and then dispersed for planting. This permits the person who plants the seeds to avoid the complexity and effort associated with handling and applying the compositions, and to merely handle and plant the treated seeds in a manner that is conventional for regular untreated seeds.

A composition can be applied to seeds by any standard seed treatment methodology, including but not limited to mixing in a container (e.g., a bottle or bag), mechanical application, tumbling, spraying, immersion, and solid matrix priming. Seed coating methods and apparatus for their application are disclosed in, for example, U.S. Pat. Nos. 5,918,413; 5,891,246; 5,554,445; 5,389,399; 5,107,787; 5,080,925; 4,759,945 and 4,465,017, among others. Any conventional active or inert material can be used for contacting seeds with the composition, such as conventional film-coating materials including but not limited to water-based film coating materials.

For example, in one embodiment, a composition can be introduced onto or into a seed by use of solid matrix priming. For example, a quantity of the composition can be mixed with a solid matrix material and then the seed can be placed into contact with the solid matrix material for a period to allow the composition to be introduced to the seed. The seed can then optionally be separated from the solid matrix material and stored or used, or the mixture of solid matrix material plus seed can be stored or planted directly. Non-limiting examples of solid matrix materials which are useful include polyacrylamide, starch, clay, silica, alumina, soil, sand, polyurea, polyacrylate, or any other material capable of absorbing or adsorbing the composition for a time and releasing the active compound of the composition into or onto the seed. It is useful to make sure that the active compound and the solid matrix material are compatible with each other. For example, the solid matrix material should be chosen so that it can release the active compound at a reasonable rate, for example over a period of minutes, hours, days, or weeks.

Imbibition is another method of treating seed with the composition. For example, a plant seed can be directly immersed for a period of time in the composition. During the period that the seed is immersed, the seed takes up, or imbibes, a portion of the composition. Optionally, the mixture of plant seed and the composition can be agitated, for example by shaking, rolling, tumbling, or other means. After imbibition, the seed can be separated from the composition and optionally dried, for example by patting or air drying.

A composition may be applied to the seeds using conventional coating techniques and machines, such as fluidized bed techniques, the roller mill method, rotostatic seed treaters, and drum coaters. Other methods, such as spouted beds may also be useful. The seeds may be pre-sized before coating. After coating, the seeds may be dried and then transferred to a sizing machine for sizing. Such procedures are generally known in the art.

If a composition is applied to the seed in the form of a coating, the seeds can be coated using a variety of methods known in the art. For example, the coating process can comprise spraying the composition onto the seed while agitating the seed in an appropriate piece of equipment such as a tumbler or a pan granulator.

In one embodiment, when coating seed on a large scale (for example a commercial scale), the seed coating may be applied using a continuous process. For example, seed may be introduced into the treatment equipment (such as a tumbler, a mixer, or a pan granulator) either by weight or by flow rate. The amount of composition that is introduced into the treatment equipment can vary depending on the seed weight to be coated, surface area of the seed, the concentration of the fungicide and/or other active ingredients in the composition, the desired concentration on the finished seed, and the like. A composition can be applied to the seed by a variety of means, for example by a spray nozzle or revolving disc. The amount of liquid may be determined by the assay of the formulation and the required rate of active ingredient necessary for efficacy. As the seed falls into the treatment equipment the seed can be treated (for example by misting or spraying with the composition) and passed through the treater under continual movement/tumbling where it can be coated evenly and dried before storage or use.

In another embodiment, the seed coating may be applied using a batch process. For example, a known weight of seeds can be introduced into the treatment equipment (such as a tumbler, a mixer, or a pan granulator). A known volume of the composition can be introduced into the treatment equipment at a rate that allows the composition to be applied evenly over the seeds. During the application, the seed can be mixed, for example by spinning or tumbling. The seed can optionally be dried or partially dried during the tumbling operation. After complete coating, the treated sample can be removed to an area for further drying or additional processing, use, or storage.

In an alternative embodiment, the seed coating may be applied using a semi-batch process that incorporates features from each of the batch process and continuous process embodiments set forth above.

In still another embodiment, seeds can be coated in laboratory size commercial treatment equipment such as a tumbler, a mixer, or a pan granulator by introducing a known weight of seeds in the treater, adding the desired amount of the composition, tumbling or spinning the seed and placing it on a tray to thoroughly dry.

In another embodiment, seeds can also be coated by placing the known amount of seed into a narrow neck bottle or receptacle with a lid. While tumbling, the desired amount of the composition can be added to the receptacle. The seed is tumbled until it is coated with the composition. After coating, the seed can optionally be dried, for example on a tray.

In some embodiments, the treated seeds may also be enveloped with a film overcoating to protect the fungicidal coating. Such overcoatings are known in the art and may be applied using conventional fluidized bed and drum film coating techniques. The overcoatings may be applied to seeds that have been treated with any of the seed treatment techniques described above, including but not limited to solid matrix priming, imbibition, coating, and spraying, or by any other seed treatment technique known in the art.

Treated Seeds

In one embodiment the disclosure is generally related to a seed that has been treated with a composition as described herein comprising a compound (e.g., a compound of Formula I, Ia, Ib, II, IIa, IIb, IIc, IId, III, or IV) as described herein. In some embodiments, the seed has been treated with the composition using one of the seed treatment methods set forth above, including but not limited to solid matrix priming, imbibition, coating, and spraying. The treated seed may be of any plant species, as described above. In other embodiments, a seed is treated with a composition as described herein, including formulating, mixing in a seed treater tank, or combining on a seed by overcoating one or more additional active ingredients. The additional active ingredient may be, for example, an additional pesticide. The pesticide may be, for example, an insecticide, a fungicide, an herbicide, or an additional nematicide as described herein.

The amount of a compound present on a treated seed sufficient to protect the seed, and/or the roots of a plant grown from the seed, against damage by phytopathogenic fungi can be readily determined by one of ordinary skill in the art. In an embodiment, treated seeds comprise a compound of Formula I, Ia, Ib, II, IIa, IIb, IIc, IId, III, or IV in an amount of at least about 0.005 mg/seed. In another embodiment, treated seeds comprise a compound of Formula I, Ia, Ib, II, IIa, IIb, IIc, IId, III, or IV in an amount of from about 0.005 to about 2 mg/seed, or from about 0.005 to about 1 mg/seed.

Having described the disclosure in detail, it will be apparent that modifications and variations are possible without departing from the scope of the claims.

Administration

In some embodiments, a compound (e.g., a compound of Formula I, Ia, Ib, II, IIa, IIb, IIc, IId, III, or IV) as described herein is used as a ACCase modulator. For example, in some embodiments, the present disclosure is directed to a method of modulating acetyl-CoA carboxylase (ACCase) in a biological organism, wherein the method comprises administering to the biological organism a composition comprising an effective amount of a compound.

In some embodiments, the biological organism is an animal. For example, in some embodiments, the biological organism is a warm-blooded animal. In some embodiments, the biological organism is a mammal, including, for example, humans.

A compound described herein may generally be formulated in a composition comprising one or more biologically acceptable excipients and, optionally, another pharmaceutically active agent known to those skilled in the art.

Any suitable dosage may be administered. The compound or salt thereof chosen for a particular application, the carrier and the amount will vary widely depending on the species of the warm blooded animal or human or the particular disease condition being treated, and depending upon the effective modulatory concentrations observed in trial studies. The dosage administered will, of course, vary depending upon known factors, such as the pharmacodynamic characteristics of the particular compound or salt thereof and its mode and route of administration; the age, health, or weight of the subject; the nature and extent of symptoms; the metabolic characteristics of the composition and patient, the kind of concurrent treatment; the frequency of treatment; or the effect desired.

A dosage unit may comprise a single compound, or mixtures thereof, with other compounds. The dosage unit may comprise diluents, extenders, carriers, liposomes, or the like. The unit may be in solid or gel form such as pills, tablets, capsules and the like or in liquid form suitable for oral, rectal, topical, intravenous injection or parenteral administration or injection into or around the treatment site.

EXAMPLES

The following non-limiting examples are provided for further illustration.

Example 1: ACCase Enzymatic Assay

*Ustilago maydis* acetyl CoA carboxylase (ACCase) was cloned, expressed, and purified as described (Weatherly et al, Biochem. J., 2004) and the test compounds were tested in a 96-well plate format. Primary in vitro screening consisted of obtaining dose response data at 100, 33, 10, and 1 μM inhibitor. Actives in the primary screen were re-tested to establish IC50 values.

Direct detection of the conversion of acetyl CoA to malonyl CoA by ACCase was not feasible, but during this process ATP is converted to ADP which allowed for detection through a standard reaction coupling with ADP recycling to the oxidation of NADH. Thus, ACCase activity was measured via kinetic OD340 measurements of the conversion of NADH to NAD in a coupled reaction involving the conversion of phosphoenolpyruvate (PEP) to lactate.

The complete 200 ul reaction mixture contained 52.5 mM HEPES (pH8), 2.625 mM $MgCl_2$, 1 mM ATP, 0.525 mM DTT, 11 mM $NaHCO_3$, 1% DMSO with or without inhibitor, 1× pyruvate kinase/lactate dehydrogenase (PK/LDH), 0.3 mM NADH, 0.5 mM PEP, and 5 μg ACCase. The reactions were incubated at 30° C. for 10 minutes and then initiated by the addition of 0.33 mM acetyl CoA. The initiated reactions were read immediately via plate reader at OD340 and kinetic readings were acquired every 20 s for 15 minutes while keeping the temperature at 30° C.

A slope of the kinetic curve was determined by using the 2 to 7 minute data which was then calculated as percent inhibition relative to the no inhibitor control.

The primary screens were conducted in duplicate and the IC50's conducted in triplicate. Averages were reported along with standard deviation calculation to generate error bars.

Each plate contained its own controls and consisted of a DMSO only control, 5-fold titration series of soraphen from 2 μM to 3.2 nM, and an ADP coupled reaction control.

In order to effectively screen out non-specific modulators of pyruvate kinase and lactate dehydrogenase (the coupled portion of the reaction), a PK/LDH inhibition test was developed. The complete 200 μl reaction mixture contained 52.5 mM HEPES (pH8), 2.625 mM $MgCl_2$, 0.525 mM DTT, 11 mM $NaHCO_3$, 1% DMSO with or without inhibitor, 1× pyruvate kinase/lactate dehydrogenase (PK/LDH), 0.3 mM NADH, and 0.5 mM PEP. The reactions were incubated at 30° C. for 10 minutes and then initiated by the addition of 66 μM ADP. The initiated reactions were read immediately via plate reader at OD340 and kinetic readings were acquired every 20 s for 15 minutes while remaining at 30° C.

A slope of the kinetic curve was determined by using the 2 to 7 minute data which was then calculated as percent inhibition relative to the no inhibitor control. Those compounds which had no significant PK/LDH inhibition at or above the IC50 in the ACCase assay, were considered to be valid modulators of only ACCase. The IC50 data for compounds disclosed herein is shown in Table 1A below.

TABLE 1A

| | | ACCase Inhibitory Activity | |
|---|---|---|---|
| Formula | Name | Structure | IC50 (μM) |
| Ia-i | 2-(4-(4-phenylquinolin-2-yl)phenoxy)acetamide | | 0.515 |

TABLE 1A-continued

ACCase Inhibitory Activity

| Formula | Name | Structure | IC50 (μM) |
|---|---|---|---|
| Ia-ii | 2-(4-(4-phenylquinolin-2-yl)phenoxy)acetic acid | 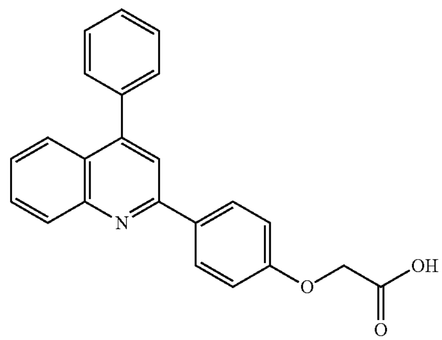 [SMILES: O=C(O)COc1ccc(-c2cc(-c3ccccc3)c3ccccc3n2)cc1] | 0.165 |
| Ia-iii | 2-(4-(8-methoxy-4-phenylquinolin-2-yl)phenoxy)acetamide | 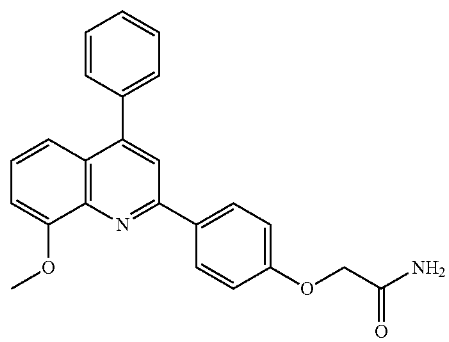 [SMILES: COc1cccc2c(-c3ccccc3)cc(-c3ccc(OCC(N)=O)cc3)nc12] | 0.549 |
| Ia-iv | 2-(4-(8-ethyl-4-phenylquinolin-2-yl)phenoxy)acetamide | 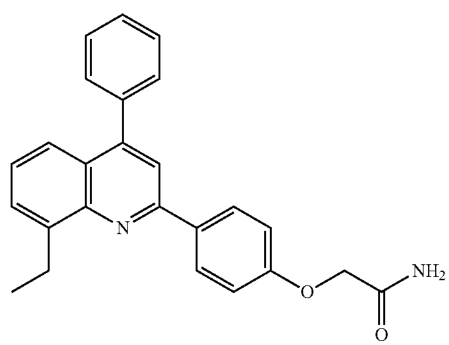 [SMILES: CCc1cccc2c(-c3ccccc3)cc(-c3ccc(OCC(N)=O)cc3)nc12] | 8.154 |
| Ia-v | 2-(4-(6-chloro-4-phenylquinolin-2-yl)phenoxy)-N-(2-hydroxyethyl)acetamide | 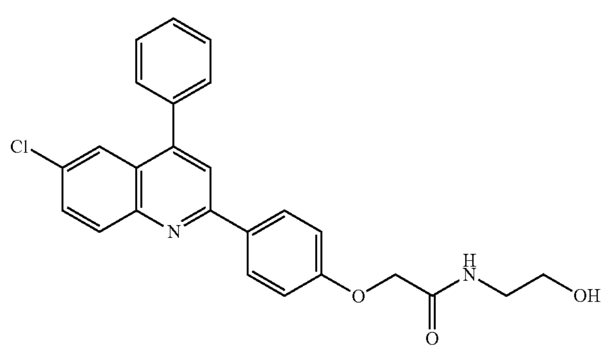 [SMILES: O=C(COc1ccc(-c2cc(-c3ccccc3)c3cc(Cl)ccc3n2)cc1)NCCO] | 13.0 |

TABLE 1A-continued

ACCase Inhibitory Activity

| Formula | Name | Structure | IC50 (μM) |
|---|---|---|---|
| Ib-i | 2-(5-(3-chloro-4-phenylquinolin-2-yl)thiophen-2-yl)acetamide | 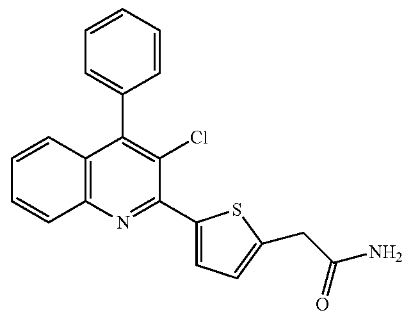 [SMILES: NC(=O)Cc1ccc(-c2nc3ccccc3c(-c3ccccc3)c2Cl)s1] | 1.32 |
| Ib-ii | 2-(5-(3-chloro-4-phenylquinolin-2-yl)thiophen-2-yl)acetic acid | 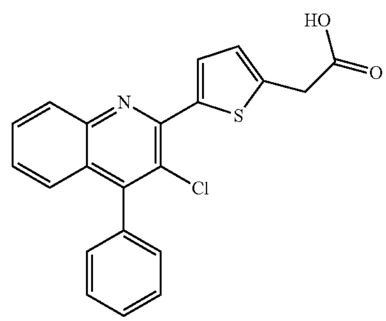 [SMILES: O=C(O)Cc1ccc(-c2nc3ccccc3c(-c3ccccc3)c2Cl)s1] | 0.110 |
| Ib-iii | 2-(5-(4-phenylquinolin-2-yl)thiophen-2-yl)acetamide | 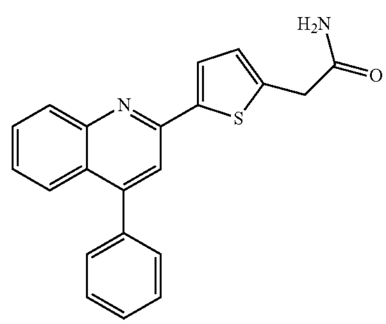 [SMILES: NC(=O)Cc1ccc(-c2cc(-c3ccccc3)c3ccccc3n2)s1] | 8.176 |
| Ib-iv | 2-(5-(4-phenylquinolin-2-yl)thiophen-2-yl)acetic acid | 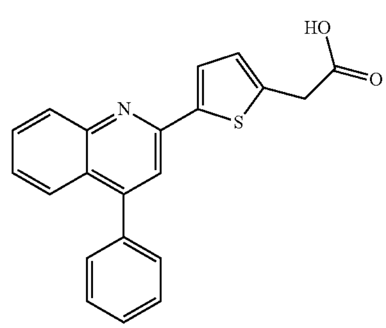 [SMILES: O=C(O)Cc1ccc(-c2cc(-c3ccccc3)c3ccccc3n2)s1] | 0.145 |

TABLE 1A-continued

ACCase Inhibitory Activity

| Formula | Name | Structure | IC50 (µM) |
|---|---|---|---|
| Ib-v | 2-(5-(8-methoxy-4-phenylquinolin-2-yl)thiophen-2-yl)acetamide | 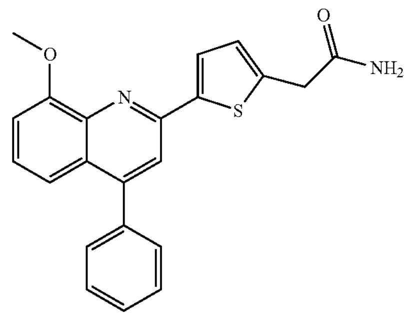 [SMILES: COc1cccc2c(-c3ccccc3)cc(-c3ccc(CC(N)=O)s3)nc12] | 4.211 |
| Ib-vi | 2-(5-(8-ethyl-4-phenylquinolin-2-yl)thiophen-2-yl)acetamide | 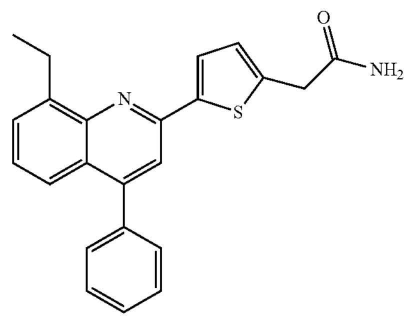 [SMILES: CCc1cccc2c(-c3ccccc3)cc(-c3ccc(CC(N)=O)s3)nc12] | 9.583 |
| IId-i | methyl 2-(5-(4-phenylquinolin-2-yl)thiophen-2-yl)acetate | 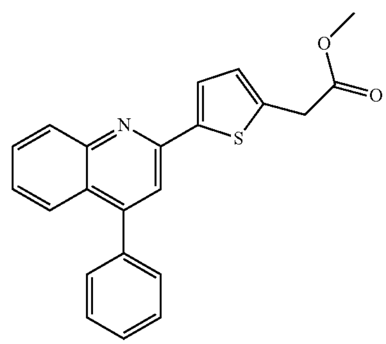 [SMILES: COC(=O)Cc1ccc(-c2cc(-c3ccccc3)c3ccccc3n2)s1] | 11.97 |
| III-i | 2-((7-methoxy-4-phenylquinolin-2-yl)thio)propanamide | 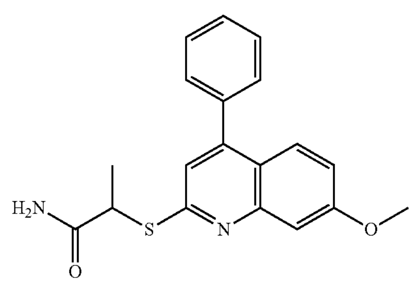 [SMILES: COc1ccc2c(-c3ccccc3)cc(SC(C)C(N)=O)nc2c1] | 8.8 |
| IV-i | 2-(4-methoxyphenyl)-4-phenylquinoline | 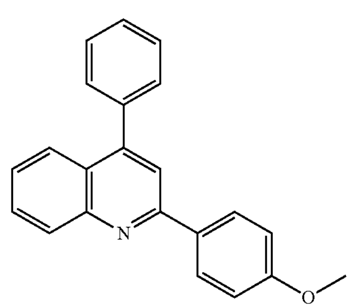 [SMILES: COc1ccc(-c2cc(-c3ccccc3)c3ccccc3n2)cc1] | 21.16 |

TABLE 1A-continued

ACCase Inhibitory Activity

| Formula | Name | Structure | IC50 (µM) |
|---|---|---|---|
| IV-ii | 2-(3,4-dimethoxyphenyl)-4-phenylquinoline | 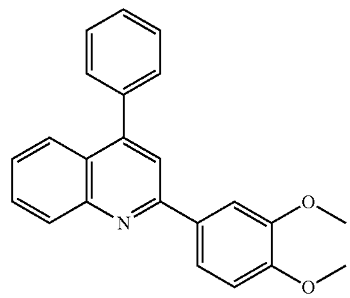 [SMILES: COc1ccc(-c2cc(-c3ccccc3)c3ccccc3n2)cc1OC] | 7.82 |
| | Soraphen | | 0.0458[a] |

[a]IC50 values are a result of two or more experiments

Example 2: Fungal Growth Inhibition Assay

Spores were isolated from previously sub-cultured plates of *Botrytis cinerea, Phytophthora capsici, Fusarium moniliforme, Fusarium viguliforme, Collectotrichum graminicola,* and *Diplodia maydis*. All spores were filtered and collected in a sterile glass bowl to isolate the spores from the mycelia. The isolation and sub-culture plate condition for each pathogen is described below.

Spore isolation for *B. cinerea*: A 2-3 week old V8 (17%)+CaCO₃ (3 g/L)+20 g agar plate was removed from room temperature and the mycelia were treated with 5-10 ml of filter sterilized Triton X 100 (0.05%). The mycelia were scraped to re-suspend the spores. The spores were then collected in a sterile filter bowl containing a fluted piece of filter paper and poured into a conical tube.

Spore isolation for *F. moniliforme*: A 1 week old PDA (potato dextrose agar, pre-mix) plate was removed from 26° C. incubator with a light/dark 12 hour cycle and the mycelia were treated with 5-10 ml of filter sterilized Triton X 100 (0.05%). The mycelia were scraped to re-suspend the spores. The spores were then collected in a sterile filter bowl containing a fluted piece of filter paper.

Spore isolation for *C. graminicola*: A 1-2 week old oatmeal agar (pre-mix) plate was removed from 26° C. incubator with a light/dark 12 hour cycle and the mycelia were treated with 10-15 ml of filter sterilized distilled water. The mycelia were scraped to re-suspend the spores. The spores were then collected in a sterile filter bowl containing a piece of sterile cheesecloth and poured into a conical tube.

Spore isolation for *F. virguliforme*: A 2-3 week old PDA (pre-mix) plate containing cefotaxime (100 mg/L) and kanamycin (50 mg/L) was removed from 26° C. incubator with a light/dark 12 hour cycle and the mycelia were treated with 5-10 ml of filter sterilized distilled water. The mycelia were scraped to re-suspend the spores. The spores were then collected in a sterile filter bowl containing a fluted piece of filter paper and poured into a conical tube.

Spore isolation for *D. maydis*: A 3-4 week old PDA (pre-mix) plate was removed from 26° C. incubator with a light/dark 12 hour cycle and the mycelia were treated with 6-7 ml of sterile distilled water, scraped into a sterile petri dish, and smashed to open the pycnidia. The spores were then collected in a sterile filter bowl containing a fluted piece of filter paper and poured into a conical tube.

Spore isolation for *P. capsici*: Three to five days prior to the assay a 2-3 week old V8 (17%)+CaCO₃ (3 g/L)+20 g agar plate was removed from a dark 25° C. incubator and cut up into small chunks. One plate was separated into two deep well plates and rinsed with sterile distilled water three times. The cut up pieces were incubated under light in a sterile filter hood with 25 ml of sterile distilled water. On the day of the assay the water was removed and 5-7 ml of fresh sterile distilled water was added. One plate was incubated at 4° C. for 45-60 minutes and then placed at room temperature for about 45-60 minutes. The spores were collected in a sterile filter bowl containing a fluted piece of filter paper. The spores were vortexed in a conical tube for 30-60 seconds to remove the flagella of the zoospores after isolation.

After spore isolation, pathogen spores were counted on a hemocytometer to calculate the spores/ml. In 17% V8 liquid media containing 3 g/L CaCO₃, isolated spores were diluted to individual concentrations based on the growth curves at 48 hours of each pathogen. The spore concentrations for each pathogen were as follows: *B. cinerea*—10,000 sp/ml; *P. capsici*—300 sp/ml; *F. monliforme*—500 sp/ml; *F. virguliforme*—500 sp/ml; *C. graminicola*—3,000 sp/ml; and *D. maydis*—3,000 sp/ml.

Chemistry stocks were dissolved in DMSO at 2.5 mg/ml. Chemistry was diluted in a 96-well stock plate in five-fold dilutions to obtain a final concentration of 50, 10, and 2 ppm in vitro. The final concentration of the positive control after the five-fold dilutions was as follows: soraphen—0.5, 0.1, and 0.02 ppm. Negative controls on each plate included 2% DMSO, water containing spores and media, and a blank for background subtraction.

In a 96-well plate the spore solution, chemistries, and controls were combined to make the final solution concentrations mentioned above. Upon addition of the chemistry, an OD600 reading was done to assess chemical precipitation. The 96-well plates were incubated in plastic tubs containing wet paper towels under the following conditions, 25° C. in the dark for *P. capsici* and *B. cinerea* or 26° C. with light/dark cycle for *C. graminicola, D. maydis, F. virguliforme, F. monliforme*. Plate readings were repeated at 24 and 48 hrs. Visual ratings were performed at 24 and 48 hrs to check for precipitation and confirm efficacy. Visual and OD600 ratings of the chemistry at 48 hours were compared to the 2% DMSO control to determine the percent of pathogen growth inhibition.

Fungal growth inhibition for compounds disclosed herein against several fungal species is shown in Table 2A through 2F.

TABLE 2A

Fungal Growth Inhibition of *Collectotrichum graminicola*

| Formula | C. graminicola % growth inhibition at 48 h | | |
|---|---|---|---|
| | 50 ppm | 10 ppm | 2 ppm |
| Ib-i | | 51 | 44 |
| Ib-ii | 78 | 67 | 0 |
| Ib-iii | 81 | 98 | 31 |
| Ib-iv | 97 | 53 | 0 |
| IId-i | 79 | 32 | 6 |
| IV-i | | 22 | 35 |
| IV-ii | | 41 | 34 |

TABLE 2B

Fungal Growth Inhibition of *Diplodia maydis*

| Formula | D. maydis % growth inhibition at 48 h | | |
|---|---|---|---|
| | 50 ppm | 10 ppm | 2 ppm |
| Ib-ii | | 70 | 55 |
| Ib-iv | 89 | 45 | 8 |
| IIc-i | | 44 | 12 |
| IId-i | | 26 | 16 |
| IId-ii | | 30 | 26 |
| IV-i | | 44 | 21 |
| IV-ii | | 34 | 26 |

TABLE 2C

Fungal Growth Inhibition of *Fusarium virguliforme*

| Formula | F. virguliforme % growth inhibition at 48 h | | |
|---|---|---|---|
| | 50 ppm | 10 ppm | 2 ppm |
| Ib-i | | 31 | 43 |
| Ib-iv | | 29 | 4 |
| Ib-ii | | 41 | 31 |
| IId-ii | | 34 | 44 |

TABLE 2D

Fungal Growth Inhibition of *Botrytis cinerea*

| Formula | B. cinerea % growth inhibition at 48 h | | |
|---|---|---|---|
| | 50 ppm | 10 ppm | 2 ppm |
| Ib-iv | 42 | 1 | 0 |

TABLE 2E

Fungal Growth Inhibition of *Phytophthora capsici*

| Formula | P. capsici % growth inhibition at 48 h | | |
|---|---|---|---|
| | 50 ppm | 10 ppm | 2 ppm |
| Ib-ii | 49 | 31 | 18 |
| Ib-iv | 80 | 11 | 0 |

TABLE 2F

Fungal Growth Inhibition of *Fusarium moniloforme*

| Formula | P. capsici % growth inhibition at 48 h | | |
|---|---|---|---|
| | 50 ppm | 10 ppm | 2 ppm |
| Ib-ii | | 45 | 39 |
| Ib-iv | 36 | 31 | 17 |

Example 3: Yeast Growth Inhibition Assay

Yeast cells (Ade2 strain) were grown in liquid YPD (1% yeast extract, 2% peptone, 2% dextrose) for 16 hours at 30° C. from previously sub-cultured plates of *Saccharomyces cerevisiae*. The OD600 of the overnight culture was checked via spectrophotometer and diluted to a concentration of $2 \times 10^4$ cells/ml.

Chemistry stocks were dissolved in DMSO to a concentration of 10 mM. Chemistry stocks were further diluted in a 96-well stock plate to obtain final concentrations of 100, 33, 10 and 1 µM in 1% DMSO. The final concentrations of the soraphen positive control were 400, 40, and 3.2 nM. The negative controls on each plate included a background subtraction control containing yeast and 1% DMSO (without chemistry) and a second contamination control containing YPD (with no yeast) and 1% DMSO (without chemistry).

98 µl liquid YPD was added to 2 µl diluted stock of DMSO per well and mixed thoroughly. After mixing, 100 µl of the diluted yeast solution was added to bring the final yeast concentration to $1 \times 10^4$ cells/ml or 2000 cells per well. An initial spectrophotometric reading at OD600 was conducted on the entire plate and served as the 0 hours time point used to subtract any background. The plate was then incubated for 24 h at 30° C. with mild shaking. At the 24 h time point all wells of the plate were re-suspended by pipette to yield a uniform suspension, then read again at OD600. The OD600 reading at 0 hours (background) was subtracted from the 24 h OD600 reading and all wells were compared to the negative control and subtracted from 100 to determine the percent inhibition. All experiments were conducted in triplicate. Averages were reported along with standard deviation calculation to generate error bars. Each plate contained its own controls and consisted of inoculated+DMSO, non-inoculated+DMSO, and a titration series of soraphen at 400, 40, and 3.2 nM. The results of growth inhibition for *Saccharomyces cerevisiae* are reported in Table 2F below.

TABLE 3

Growth Inhibition of *Saccharomyces cerevisiae*

| Formula | S. cerevisiae % growth inhibition at 48 h | | | |
|---|---|---|---|---|
| | 100 µM | 33.3 µM | 11.1 µM | 3.7 µM |
| Ib-ii | 79 | 55 | 0 | 0 |
| Ib-iii | 99 | 57 | 14 | 0 |
| Ib-iv | 99 | 15 | 0 | 0 |

Description of Synthesis

The compounds of Formulas I, Ia, Ib, II, IIa, IIb, IIc, IId, III, and IV may be prepared using methods known to those skilled in the art.

Example 4: Description of Synthesis of Compounds of Formula Ia

For example, the compounds of Formula Ia can be prepared as set forth in Scheme 1 below. More particularly, the optionally substituted 2-aminobenzophenone 1 may be reacted with 4-hydroxyacetophenone in the presence of citric acid at 120° C. to yield the desired 4-phenylquinoline derivative 3. Alkylation of the compound 3 with chloroacetamide 4 in the presence of potassium carbonate in acetone affords the desired compound of the Formula Ia where Y is $NH_2$, X is O, and substituents $R^3$ to $R^6$ are as defined with respect to Formula Ia above.

Scheme 1: Synthetic scheme for the preparation of compounds of Formula Ia

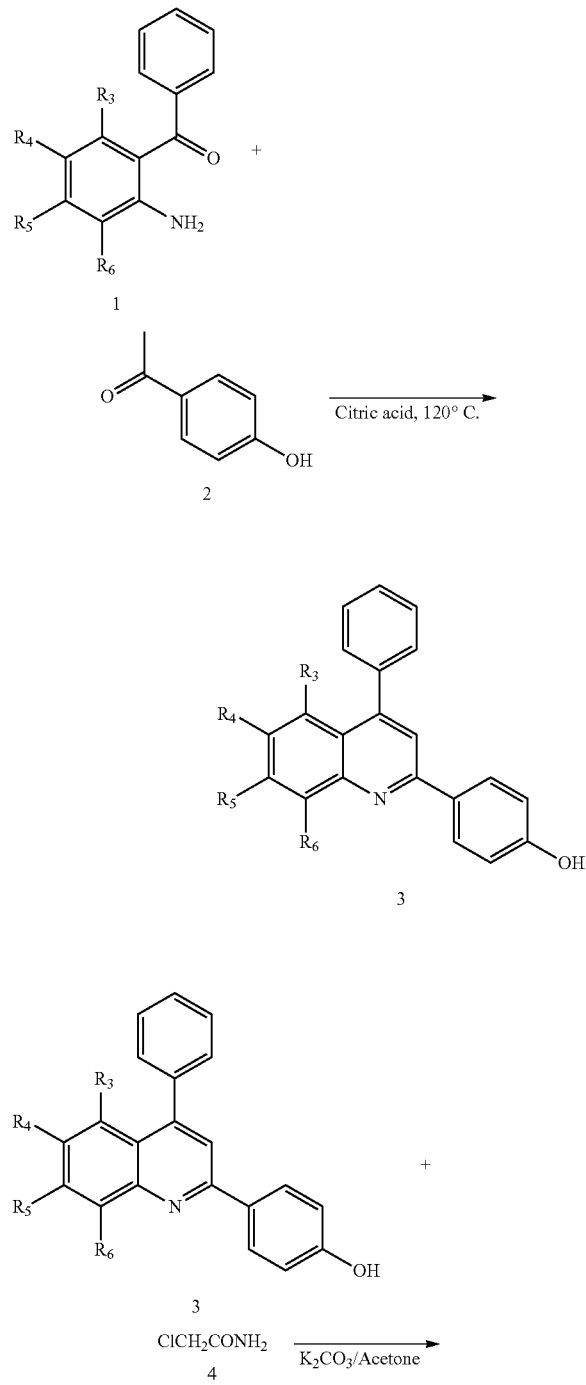

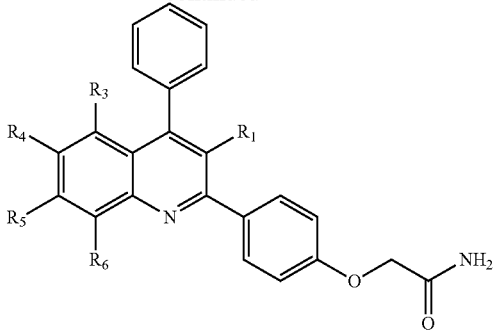

The 2-aminobenzophenone 1 described above can be prepared according to the general synthetic route depicted in Scheme 2. The optionally substituted 2-aminobenzoic acid 2 is cyclized to corresponding benzoxazine 3 by heating in acetic anhydride. Then, the compound 3 is reacted with phenylmagnesium bromide to give the corresponding N-acetyl 2-amino benzophenone which is subsequently treated with 6NHCl in ethanol to remove the acetyl group and yield the desired 2-aminobenzophenone 1.

Scheme 2: Synthetic scheme for the preparation of 2-aminobenzophenone

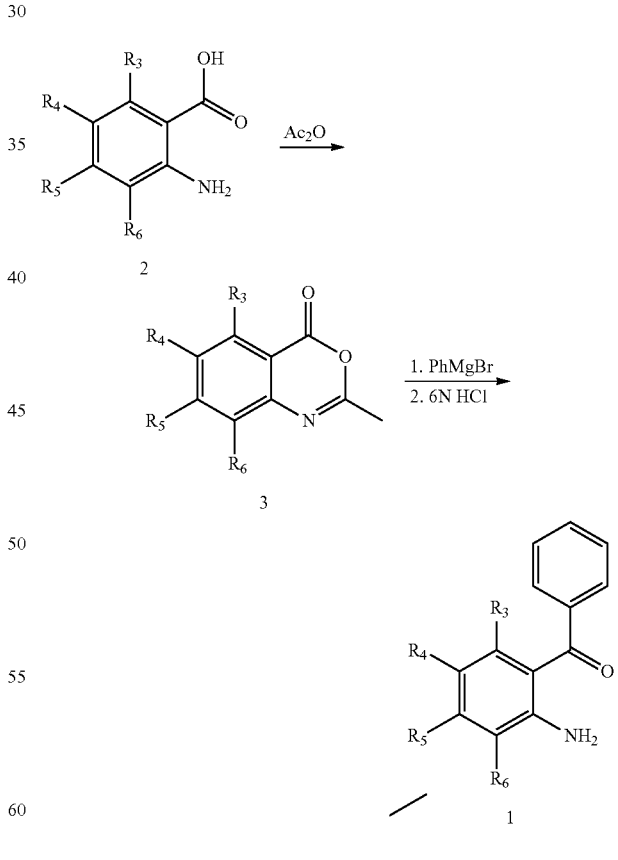

Alternatively, the compounds of Formula Ia may be prepared using the general procedure illustrated in Scheme 3, below. More particularly, preparation of a 4-phenylquinoline 3 may be accomplished using a procedure similar to that described in Scheme 1, above. In the next step, alkylation may be carried out with methyl α-bromoacetate 4 to afford the corresponding methyl ester. The saponification of the methyl ester 5 with 1 NaOH in a mixture of THF and MeOH yields the corresponding quinolinylphenoxyacetic acid 6, wherein substituents $R^3$ to $R^6$ may be selected as defined above with regard to Formula Ia.

Scheme 3: Synthesis scheme for the preparation of compounds of Formula Ia

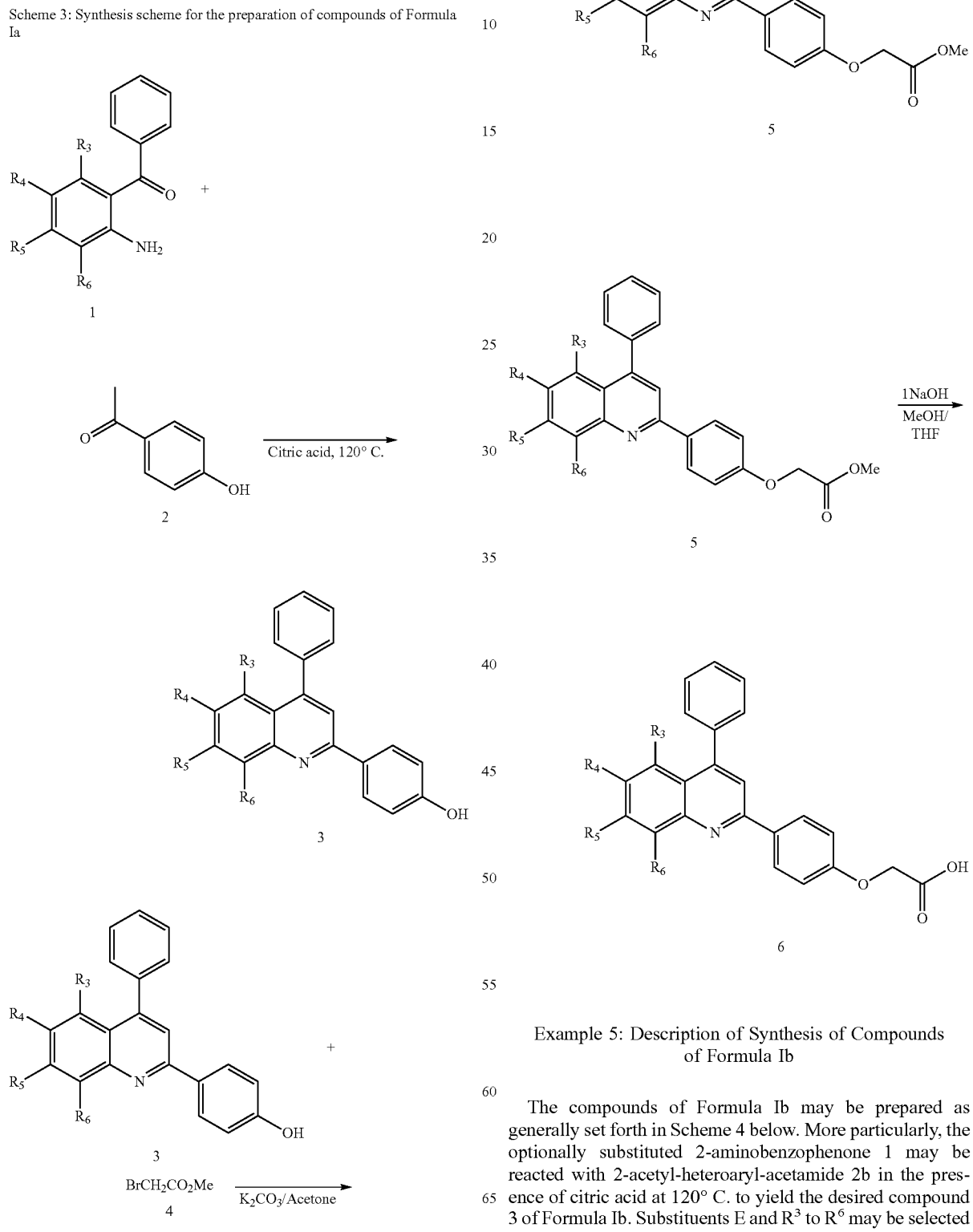

Example 5: Description of Synthesis of Compounds of Formula Ib

The compounds of Formula Ib may be prepared as generally set forth in Scheme 4 below. More particularly, the optionally substituted 2-aminobenzophenone 1 may be reacted with 2-acetyl-heteroaryl-acetamide 2b in the presence of citric acid at 120° C. to yield the desired compound 3 of Formula Ib. Substituents E and $R^3$ to $R^6$ may be selected as defined with respect to Formula Ib above.

Scheme 4: Synthetic scheme for the preparation of compounds of Formula Ib

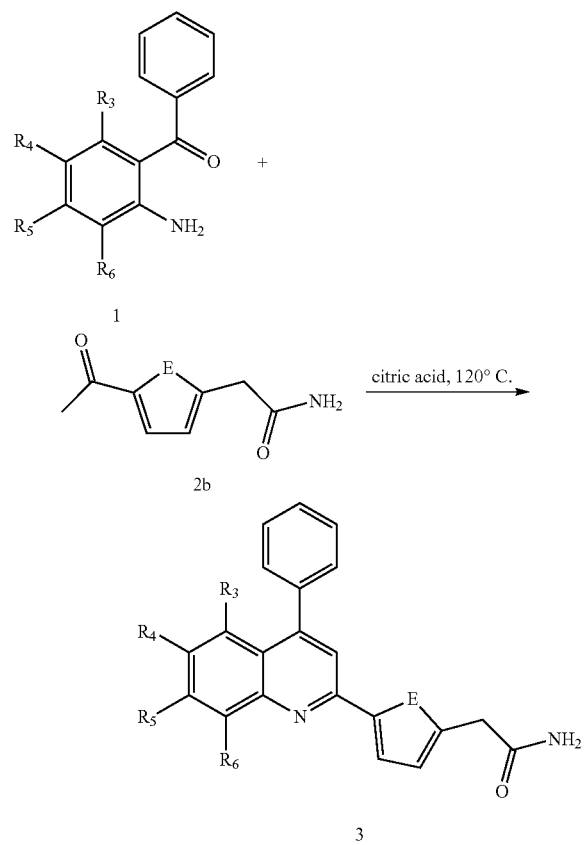

The required acetyl-heteroaryl acetic acid derivative 2b may be prepared, for example, as generally illustrated in Scheme 5 below.

Scheme 5: Synthetic scheme to acetyl-heteroaryl actetic acid derivatives

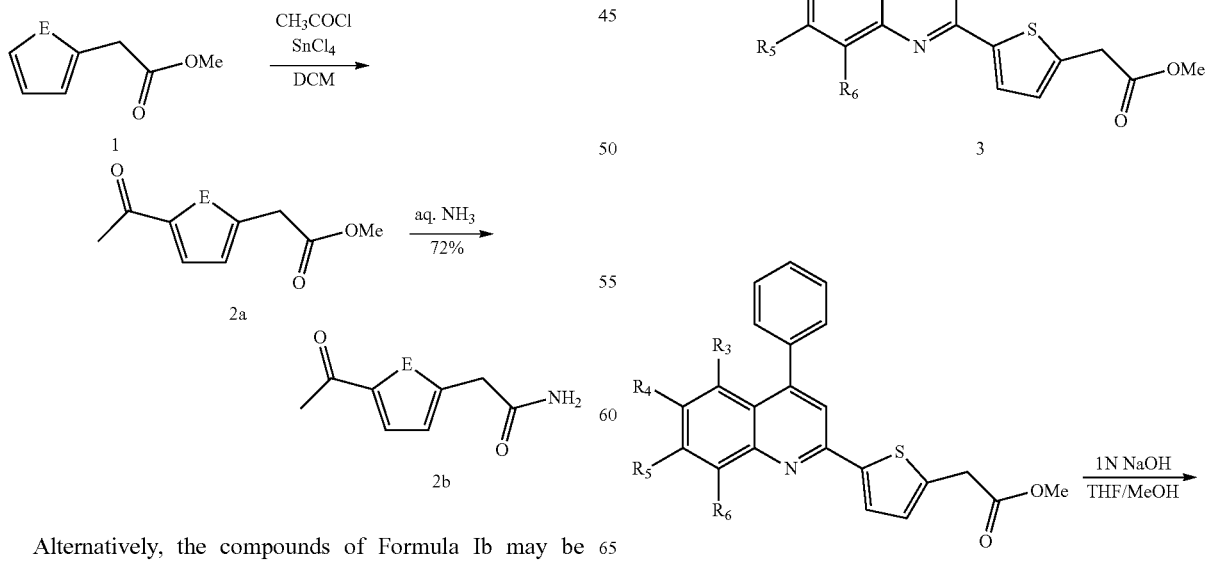

Alternatively, the compounds of Formula Ib may be prepared as generally illustrated in Scheme 6 below. More particularly, preparation of the 4-phenylquinoline derivative 3 may be accomplished by reacting of the optionally substituted 2-aminobenzophenone 1 with methyl 2-acetyl-heteroaryl-acetate 2b in the presence of citric acid at 120° C. The saponification of the methyl ester 3 with 1 NaOH in a mixture of THF and MeOH yields the corresponding acid 4. Substituents E and $R^3$ to $R^6$ may be selected as defined with respect to Formula Ib above.

Scheme 6: Synthesis scheme for the preparation of compounds of Formula Ib

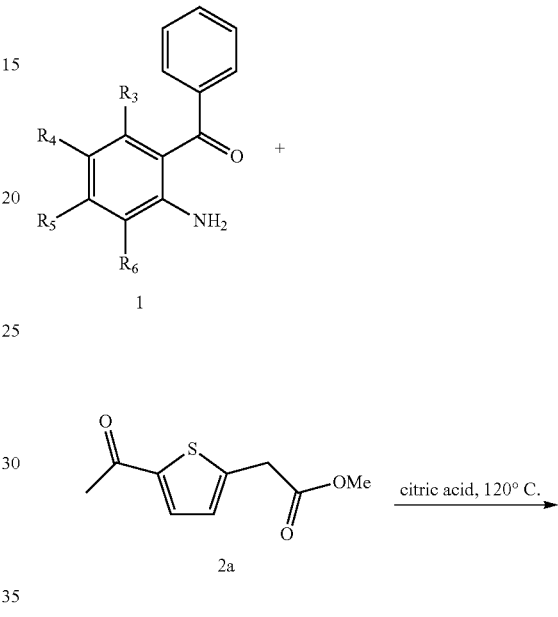

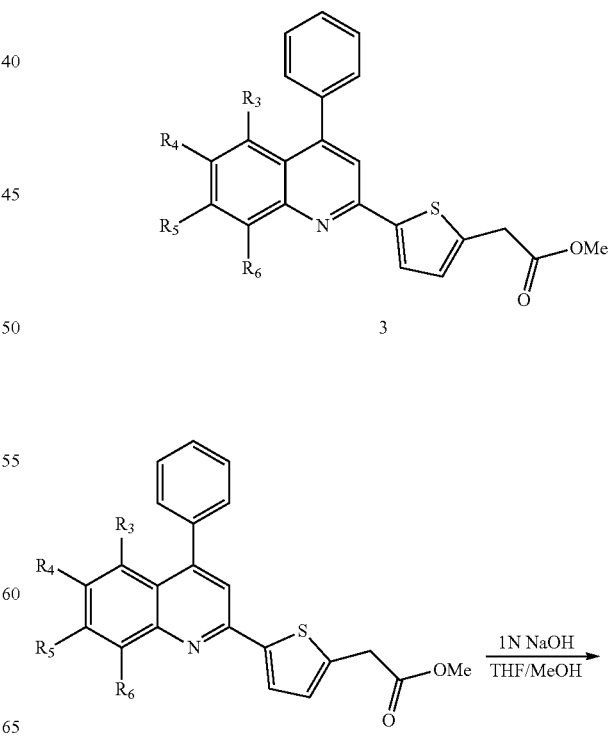

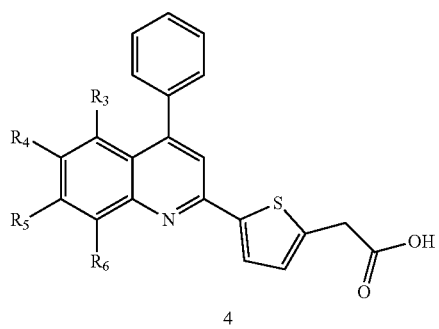
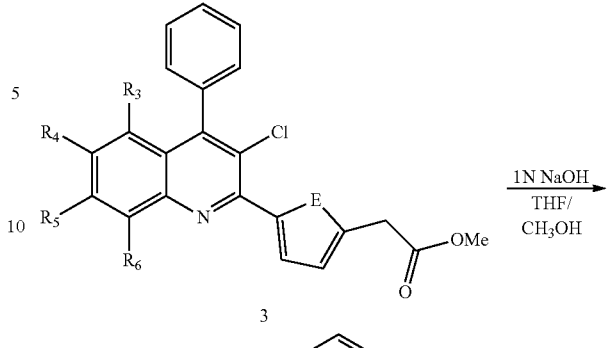

In a further alternative, the compounds of Formula Ib may be prepared as generally illustrated in Scheme 7 below. More particularly, preparation of the 4-phenylquinoline derivative 3 may be accomplished by reacting of the optionally substituted 2-aminobenzophenone 1 with 2-chloroacetyl-heteroaryl-acetate 2c in the presence of trimethylsilyl chloride (TMS-Cl). The saponification of the methyl ester 3 with 1N NaOH in a mixture of THF and MeOH yields the corresponding acid 4. Alternatively, ammonolysis of the ester 3 with NH₃ in MeOH yields the corresponding amide 5. Substituents E and $R^3$ to $R^6$ may be selected as defined with respect to Formula Ib above.

Scheme 7: Synthesis scheme for the preparation of compounds of Formula Ib

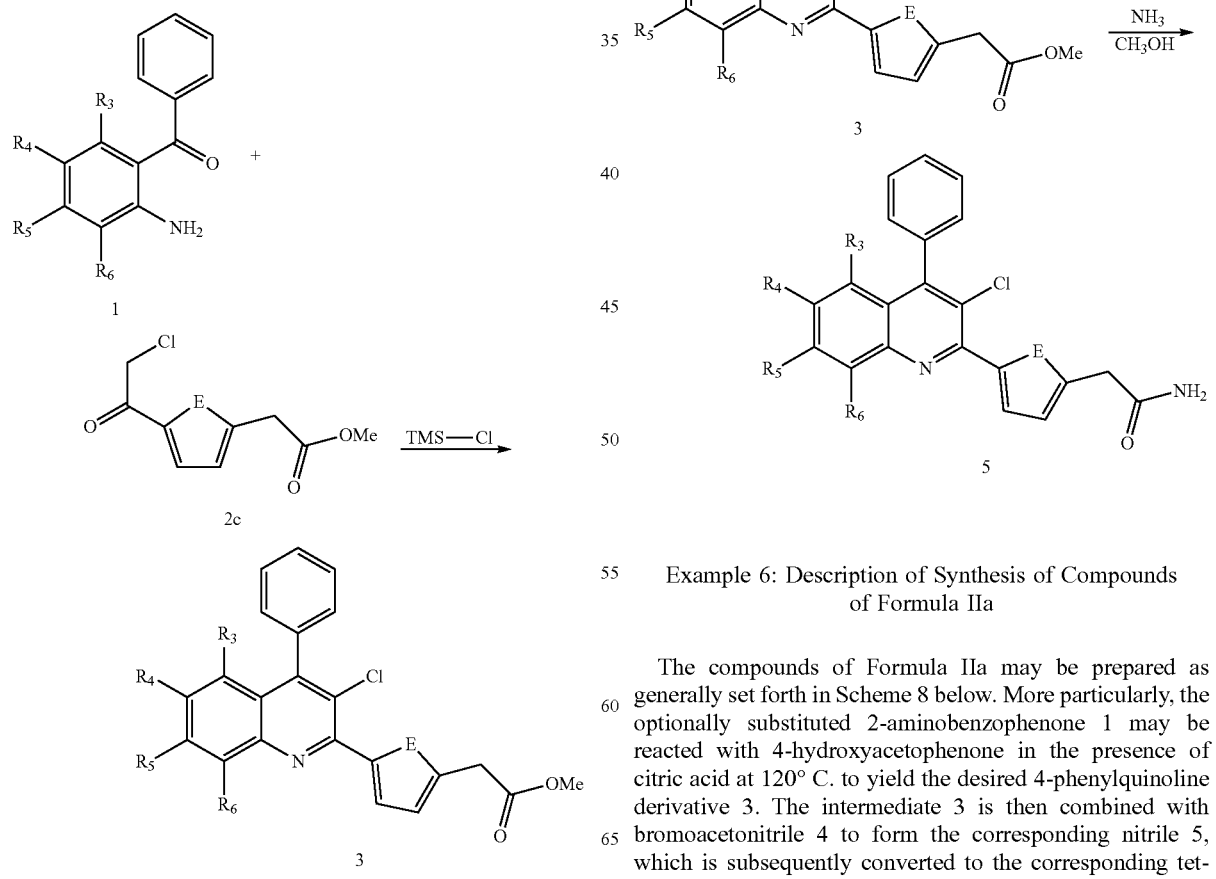

Example 6: Description of Synthesis of Compounds of Formula IIa

The compounds of Formula IIa may be prepared as generally set forth in Scheme 8 below. More particularly, the optionally substituted 2-aminobenzophenone 1 may be reacted with 4-hydroxyacetophenone in the presence of citric acid at 120° C. to yield the desired 4-phenylquinoline derivative 3. The intermediate 3 is then combined with bromoacetonitrile 4 to form the corresponding nitrile 5, which is subsequently converted to the corresponding tetrazole 5 with sodium azide in the presence of ammonium chloride in N,N-dimethylformamide (DMF). Substituents E and $R^3$ to $R^6$ may be selected as defined with respect to Formula IIa above.

Scheme 8: Synthesis scheme for the preparation of compounds of Formula IIa

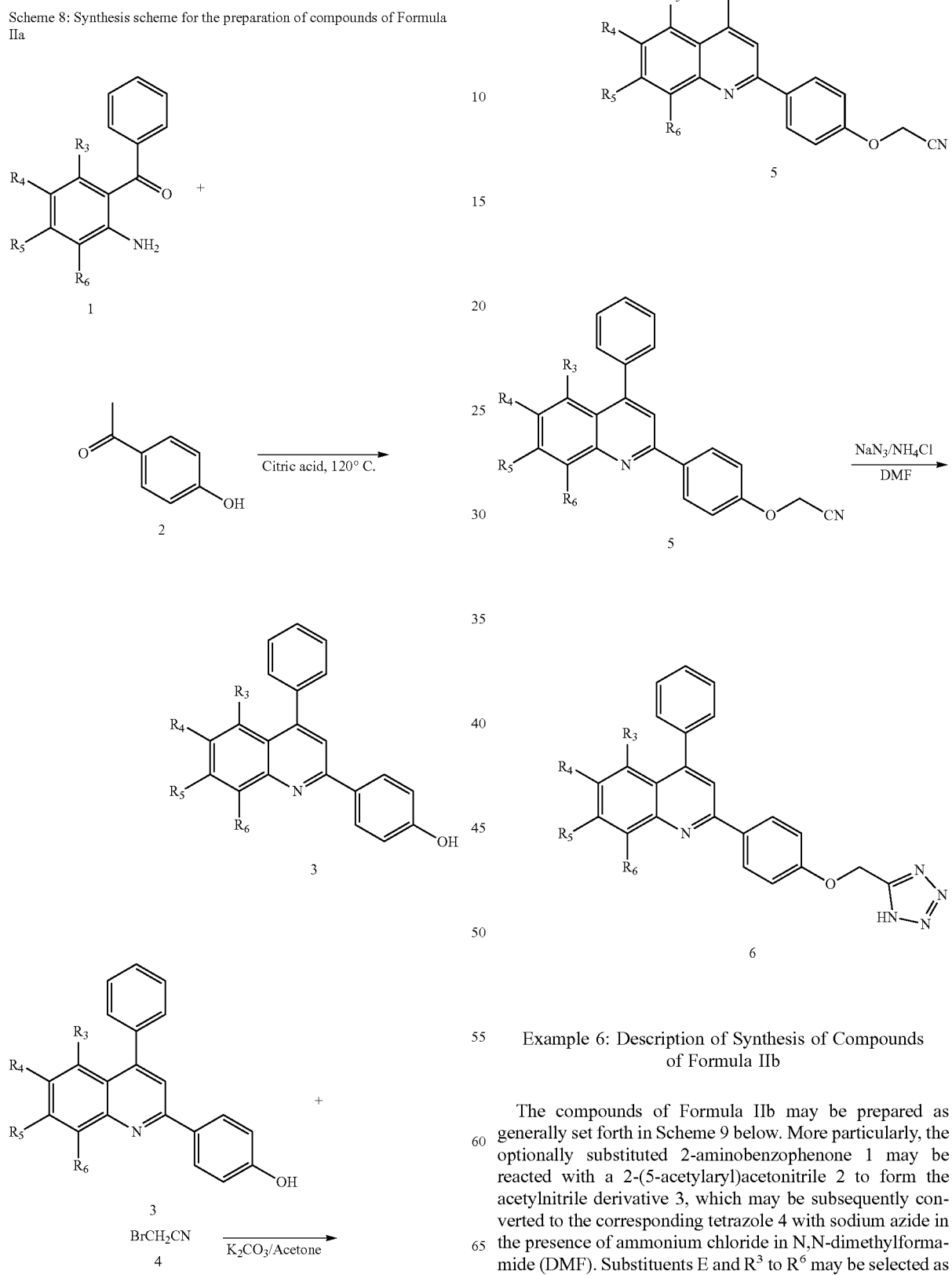

Example 6: Description of Synthesis of Compounds of Formula IIb

The compounds of Formula IIb may be prepared as generally set forth in Scheme 9 below. More particularly, the optionally substituted 2-aminobenzophenone 1 may be reacted with a 2-(5-acetylaryl)acetonitrile 2 to form the acetylnitrile derivative 3, which may be subsequently converted to the corresponding tetrazole 4 with sodium azide in the presence of ammonium chloride in N,N-dimethylformamide (DMF). Substituents E and $R^3$ to $R^6$ may be selected as defined with respect to Formula IIb above.

Scheme 9: Synthesis scheme for the preparation of compounds of Formula IIb

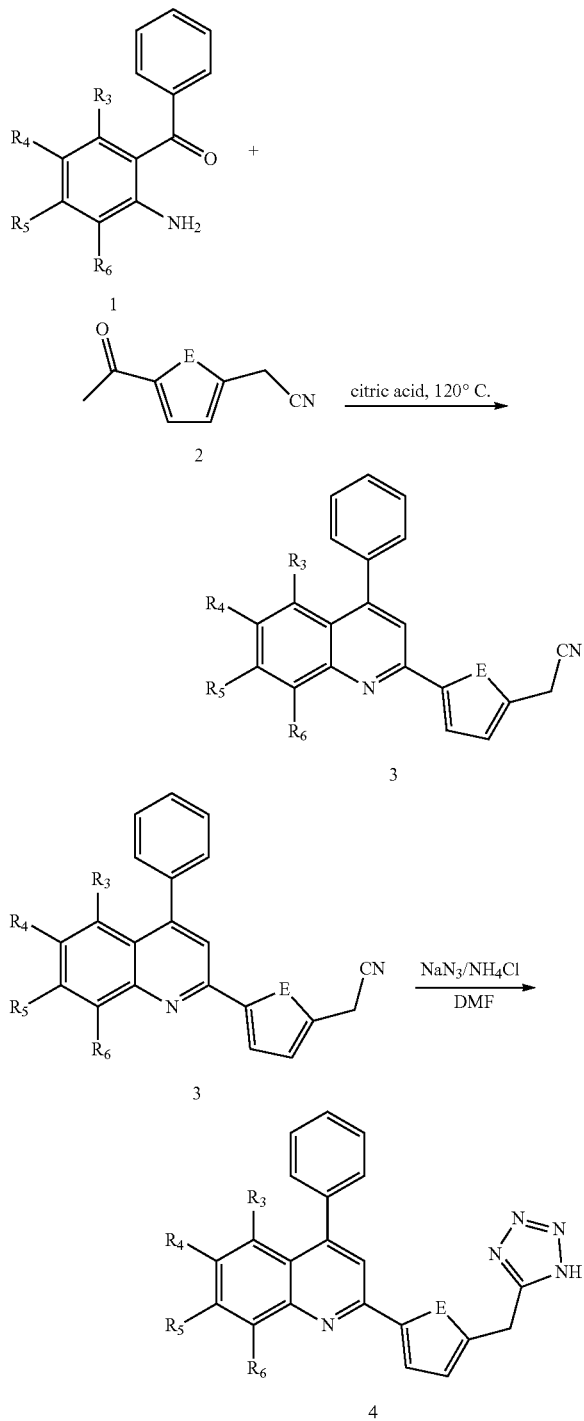

Example 7: Preparation of 2-aminobenzophenones

The intermediate compounds (2-amino-3-ethylphenyl)(phenyl)methanone and (2-amino-3-methoxyphenyl)(phenyl)methanone were prepared using the procedures set forth below.

Preparation of (2-amino-3-ethylphenyl)(phenyl)methanone

A mixture of 2-amino-3-ethylbenzoic acid (2.9 g, 17.6 mmol) and acetic anhydride (10 mL) was refluxed for 3 hours. It was cooled to room temperature and the precipitate was filtered off and washed with heptane (50 mL) and dried in vacuo to give 8-ethyl-2-methyl-4H-benzo[d][1,3]oxazin-4-one (1.84 g, 9.7 mmol, 55%) as a tan solid. The filtrate was concentrated and the residue was purified by automated column chromatography on the ISCO-companion (SiO$_2$, gradient heptane/ethyl acetate) to give an additional amount of the desired product (560 mg, 3.0 mmol, 17%) as an off-white solid. Total yield: 2.4 g, 12.7 mmol, 72%. The $^1$H-NMR spectrum was in accordance with the chemical structure.

To a solution of 8-ethyl-2-methyl-4H-benzo[d][1,3]oxazin-4-one (2.4 g, 12.7 mmol) in a mixture of benzene (10 mL) and THF (3 mL) a 2.8M solution of phenylmagnesium bromide in Et$_2$O (4.0 mL, 11.0 mmol) was added slowly. After complete addition the mixture was refluxed for 3 hours under a N$_2$-atmosphere. Then, it was cooled to room temperature and 2 M HCl (50 mL) and ethyl acetate (50 mL) were added. The layers were separated and the aqueous mixture was extracted with ethyl acetate (25 mL). The combined organic layers were washed with 2M aq. NaOH (25 mL) and brine (25 mL) and dried over Na$_2$SO$_4$. The solvent was evaporated in vacuo to give an orange oil. This was taken up in EtOH (30 mL) and 6M HCl (18 mL). The mixture was refluxed for 2 d and concentrated in vacuo. The residue was taken up in a mixture of 25% aq. NH$_3$ (25 mL) and ethyl acetate (25 mL). The layers were separated and the aqueous layer was extracted with ethyl acetate (25 mL). The combined organic layers were washed with brine (25 mL) and dried over Na$_2$SO$_4$. The solvent was evaporated in vacuo. The residue was purified by automated column chromatography on the ISCO-companion (SiO$_2$, gradient heptane/ethyl acetate) to give (2-amino-3-ethylphenyl)(phenyl)methanone (950 mg, 4.2 mmol, yield 35%) as a yellow oil. The $^1$H-NMR spectrum was in accordance with the chemical structure.

Preparation of (2-amino-3-methoxyphenyl)(phenyl)methanone

A mixture of 2-amino-3-methoxybenzoic acid (5.0 g, 29.9 mmol) and acetic anhydride (15 mL) was refluxed for 3 hours. It was cooled to room temperature and the precipitate was filtered off and washed with heptane (3×25 mL) and dried in vacuo to give 8-methoxy-2-methyl-4H-benzo[d][1,3]oxazin-4-one (4.1 g, 21.4 mmol, yield 72%) as a tan solid. $^1$H-NMR spectrum was in accordance with the chemical structure.

Conversion of 8-Methoxy-2-methyl-4H-benzo[d][1,3]oxazin-4-one (3.1 g, 16.2 mmol) with 2.8 M phenylmagnesium bromide in Et$_2$O (as described for the corresponding compound in the procedure above) afforded (2-amino-3-methoxyphenyl)(phenyl)methanone with a yield of 32% (1.18 g, 5.2 mmol) as a yellow solid. The $^1$H-NMR spectrum was in accordance with the chemical structure.

Example 8: Preparation of 2-(4-(4-phenylquinolin-2-yl)phenoxy)acetamide (Formula Ia-i)

A mixture of 2-aminobenzophenone (197 mg, 1.0 mmol), 4'-hydroxyacetophenone (150 mg, 1.1 mmol) and citric acid (96 mg, 0.50 mmol) were heated for 8 hours to 100° C.

(sandbath). The crude mixture was taken up in $CH_2Cl_2$ (1 mL) and submitted to automated column chromatography on the ISCO-companion ($SiO_2$, gradient ethyl acetate/heptane) to give 4-(4-phenylquinolin-2-yl)phenol with a 50% yield (150 mg, 0.5 mmol) as a white solid. The $^1$H-NMR spectrum was in accordance with the chemical structure.

A mixture of 4-(4-phenylquinolin-2-yl)phenol (150 mg, 0.5 mmol), $K_2CO_3$ (138 mg, 1.0 mmol), a catalytic amount of KI and chloroacetamide (129 mg, 0.55 mmol) in acetone was refluxed for 18 hours. The mixture was filtered and the filtrate was concentrated in vacuo. The residue was stirred in ethyl acetate (3 mL), filtered and washed with ethyl acetate (2 ml) and dried in air to give 2-(4-(4-phenyl-quinolin-2-yl)phenoxy)acetamide with a 48% yield (85 mg, 0.24 mmol, 48%) as an off-white solid with an HPLC purity of 99.5%. LC-MS [M+H] 355 ($C_{23}H_{18}N_2O_2$+H, expected 355.1). The $^1$H-NMR spectrum was in accordance with the chemical structure.

Example 9: Preparation of 2-(4-(4-phenylquinolin-2-yl)phenoxy)acetic acid (Formula Ia-ii)

A mixture of methyl 2-(4-(4-phenylquinolin-2-yl)phenoxy)acetate (prepared as described in Example 20, below) (74 mg, 0.2 mmol), MeOH (1 mL), THF (1 mL) and 2N NaOH (1 mL) was stirred for 6 hours at room temperature. TLC-control showed complete conversion and the organic solvent was removed in vacuo. The pH of the aqueous residue was cautiously adjusted to 7-8 with 1 N HCl. The solid was filtered, washed with $H_2O$ (3×10 mL) and dried in air to give 2-(4-(4-phenylquinolin-2-yl)phenoxy)acetic acid (60 mg, 0.169 mmol, 84%) as a tan solid with an HPLC purity of 98.0%. LC-MS [M+H] 356 ($C_{23}H_{17}NO3$+H, expected 356.1). The $^1$H-NMR spectrum was in accordance with the chemical structure.

Example 10: Preparation of 2-(4-(8-methoxy-4-phenylquinolin-2-yl)phenoxy)acetamide (Formula Ia-iii)

A mixture of (2-amino-3-methoxyphenyl)(phenyl)methanone (93 mg, 0.41 mmol), 4'-hydroxyacetophenone (61 mg, 0.45 mmol) and citric acid (39 mg, 0.205 mmol) was heated for 18 hours to 120° C. (sandbath). The crude mixture was taken up in ethyl acetate (20 mL) and washed with $H_2O$ (10 mL) and brine (10 ml) and dried over $Na_2SO_4$. The solvent was evaporated in vacuo and the residue was purified by automated column chromatography on the ISCO-companion ($SiO_2$, gradient ethyl acetate/heptane) to give 4-(8-methoxy-4-phenylquinolin-2-yl)phenol (64 mg, 0.195 mmol, 48%) as an off-white solid. The $^1$H-NMR spectrum was in accordance with the chemical structure.

A mixture of 4-(8-methoxy-4-phenylquinolin-2-yl)phenol (64 mg, 0.195 mmol), $K_2CO_3$ (54 mg, 0.39 mmol), a catalytic amount of KI and chloroacetamide (18 mg, 0.2 mmol) in acetone (10 mL) was refluxed for 18 hours. Conversion was complete yet and the same amounts of $K_2CO_3$ (54 mg, 0.39 mmol) and chloroacetamide (18 mg, 0.2 mmol) were added. Reflux was continued for 24 hours. The mixture was filtered, the filtrate rinsed with ethyl acetate (20 mL) and the filtrate was concentrated in vacuo. The residue was purified by automated column chromatography on the ISCO-companion ($SiO_2$, gradient ethyl acetate/heptane) to give 2-(4-(8-methoxy-4-phenylquinolin-2-yl)phenoxy)acetamide (28 mg, 0.073 mmol, 37%) as an off-white solid with an HPLC purity of 99.8%. LC-MS [M+H] 385 ($C_{24}H_{20}N_2O_3$+H, expected 385.15). The $^1$H-NMR spectrum was in accordance with the chemical structure.

Example 11: Preparation of 2-(4-(8-ethyl-4-phenylquinolin-2-yl)phenoxy)acetamide (Formula Ia-iv)

A mixture of (2-Amino-3-ethylphenyl)(phenyl)methanone (112 mg, 0.5 mmol), 4'-hydroxyacetophenone 4 (75 mg, 0.55 mmol) and citric acid (48 mg, 0.25 mmol) was heated for 20 hours to 120° C. (sandbath). The crude mixture was taken up in ethyl acetate (20 mL) and washed with sat. $NaHCO_3$ (10 mL) and brine (10 ml) and dried over $Na_2SO_4$. The solvent was evaporated in vacuo and the residue was purified by automated column chromatography on the ISCO-companion ($SiO_2$, gradient ethyl acetate/heptane) to give 4-(8-ethyl-4-phenylquinolin-2-yl)phenol (68 mg, 0.209 mmol, 42%) as a pink solid. The $^1$H-NMR spectrum was in accordance with the chemical structure.

A mixture of 4-(8-Ethyl-4-phenylquinolin-2-yl)phenol (68 mg, 0.209 mmol), $K_2CO_3$ (58 mg, 0.42 mmol), a catalytic amount of KI and chloroacetamide (39 mg, 0.209 mmol) in acetone (10 mL) was refluxed for 18 hours. The mixture was filtered, the filtrate rinsed with ethyl acetate (20 mL) and the filtrate was concentrated in vacuo to give 2-(4-(8-Ethyl-4-phenylquinolin-2-yl)phenoxy)acetamide (34 mg, 0.089 mmol, 42%) as an off-white solid with an HPLC purity of 99.8%. LC-MS [M+H] 383.2 ($C_{25}H_{22}N_2O_2$+H, expected 383.17). The $^1$H-NMR spectrum was in accordance with the chemical structure.

Example 12: Preparation of 2-(5-acetylthiophen-2-yl)acetic acid derivatives

The intermediate compounds methyl 2-(5-acetylthiophen-2-yl)acetate and 2-(5-acetylthiophen-2-yl)acetamide were prepared using the procedures set forth below.

Preparation of methyl 2-(5-acetylthiophen-2-yl)acetate

A solution of methyl 2-(thiophen-2-yl)acetate (12.5 g, 80.0 mmol) in $CH_2Cl_2$ (300 mL) was cooled to 0° C. Acetyl chloride (5.8 mL, 6.4 g, 81.2 mmol) was added, followed by the dropwise addition of $SnCl_4$ (32.0 mL, 71.0 g, 272.0 mmol). After complete addition the mixture was stirred for 2 hours at 0° C. and 6M HCl (100 mL) was added. The layers were separated and the aqueous layer was extracted with TBME (3×100 mL). The combined organic layers were washed with sat. $NaHCO_3$ (100 mL) and brine (100 mL) and dried over $Na_2SO_4$. The solvent was evaporated in vacuo to give methyl 2-(5-acetylthiophen-2-yl)acetate (15.0 g, 75.7 mmol, 95%) as a yellow oil, that solidified upon standing. The $^1$H-NMR spectrum was in accordance with the chemical structure.

Preparation of 2-(5-acetylthiophen-2-yl)acetamide

A mixture of methyl 2-(5-acetylthiophen-2-yl)acetate (2.0 g, 10.1 mmol) and conc. $NH_3$ (10 mL) was stirred at room temperature; additional conc. $NH_3$ (10 mL) to facilitate stirring, which was continued overnight. The mixture was filtered, the solid was washed with $H_2O$ (3×50 mL) and dried in air to give 2-(5-Acetylthiophen-2-yl)acetamide (1.33 g, 7.3 mmol, 72%) as a grey solid. The $^1$H-NMR spectrum was in accordance with the chemical structure.

Example 13: Preparation of 2-(5-(4-phenylquinolin-2-yl)thiophen-2-yl)acetamide (Formula Ib-iii)

A mixture of 2-aminobenzophenone (200 mg, 0.41 mmol), 2-(5-acetylthiophen-2-yl)acetamide (61 mg, 0.33 mmol) and citric acid (96 mg, 0.5 mmol) was heated for 18 hours to 120° C. (sandbath). The crude mixture was taken up in ethyl acetate (20 mL) and washed with sat. $NaHCO_3$ (10 mL) and brine (10 ml) and dried over $Na_2SO_4$. The solvent was evaporated in vacuo and the residue was purified by automated column chromatography on the ISCO-companion ($SiO_2$, gradient ethyl acetate/heptane) to give 2-(5-(4-phenylquinolin-2-yl)thiophen-2-yl)acetamide in a 33% yield (37 mg, 0.108 mmol, 33%) as an off-white solid with an HPLC purity 99.7%. LC-MS [M+H] 345 ($C_{21}H_{16}N_2OS+H$, expected 345.1). The $^1$H-NMR spectrum was in accordance with the chemical structure.

Example 14: Preparation of 2-(5-(3-chloro-4-phenylquinolin-2-yl)thiophen-2-yl)acetamide (Formula Ib-i)

A mixture of methyl 2-(5-(3-chloro-4-phenylquinolin-2-yl)thiophen-2-yl)acetate (prepared as described in Example 17) (66 mg, 0.168 mmol) in 7N $NH_3$ in MeOH (10 mL) was heated for 18 h to 100° C. in a pressure tube. It was cooled to room temperature and the solvent was evaporated in vacuo. The residue was purified by automated column chromatography on the ISCO-companion ($SiO_2$, $CH_2Cl_2$/MeOH) to give the slightly impure product. After stirring overnight in $Et_2O$ (10 ml), the solid was filtered off and dried in air to give 2-(5-(3-chloro-4-phenylquinolin-2-yl)thiophen-2-yl)acetamide (35 mg, 0.09 mmol, yield 53%) as an off-white solid with an HPLC purity 96.5%. LC-MS [M+H] 379/381 ($C_{21}H_{15}C_1N_2OS+H$, expected 379.1/381.1). The $^1$H-NMR spectrum was in accordance with the chemical structure.

Example 15: Preparation of 2-(5-(4-phenylquinolin-2-yl)thiophen-2-yl)acetic acid (Formula Ib-iv)

A mixture of methyl 2-(5-(4-phenylquinolin-2-yl)thiophen-2-yl)acetate (prepared as described in Example 16) (65 mg, 0.188 mmol), MeOH (1 mL), THF (1 mL) and 2 M NaOH (1 mL) was stirred for 6 hours at room temperature. TLC-control showed complete conversion and the organic solvent was removed in vacuo. The pH of the aqueous residue was adjusted to 6 with 1M HCl. The solid was filtered, washed with $H_2O$ (3×10 mL) and dried in air to give 2-(5-(4-Phenylquinolin-2-yl)thiophen-2-yl)acetic acid (38 mg, 0.11 mmol, yield 58%) as an orange solid with an HPLC purity 86.4%. LC-MS [M+H] 346.2 ($C_{21}H_{14}C_1NO_2S+H$, expected 346.08). The $^1$H-NMR spectrum was in accordance with the chemical structure.

Example 16: Preparation of methyl 2-(5-(4-phenylquinolin-2-yl)thiophen-2-yl)acetate (Formula IId-i)

A mixture of 2-aminobenzophenone (200 mg, 1.0 mmol), methyl 2-(5-acetylthiophen-2-yl)acetate (100 mg, 0.51 mmol) and citric acid (96 mg, 0.5 mmol) was heated for 24 hours to 120° C. (sandbath). The crude mixture was taken up in $CH_2Cl_2$ (2 mL) and submitted to automated column chromatography on the ISCO-companion ($SiO_2$, gradient ethyl acetate/heptane) to give methyl 2-(5-(4-phenylquinolin-2-yl)thiophen-2-yl)acetate (75 mg, 0.209 mmol, yield 41%) as a brown oil with an HPLC purity 95.9%. LC-MS [M+H] 360 ($C_{22}H_{17}NO_2S+H$, expected 360.1). The $^1$H-NMR spectrum was in accordance with the chemical structure.

Example 17: Preparation of methyl 2-(5-(3-chloro-4-phenylquinolin-2-yl)thiophen-2-yl)-acetate (Formula IId-ii)

A mixture of 2-aminobenzophenone (340 mg, 1.72 mmol) and methyl 2-(5-(2-chloroacetyl)thiophen-2-yl)acetate (400 mg, 1.72 mmol) in DMF (3.5 mL) was transferred to a pressure-tube. $Me_3SiCl$ (1.09 mL, 934 mg, 8.6 mmol) was added and the tube was thoroughly sealed. The mixture was heated for 6 h to 100° C. It was cooled to room temperature and poured into $H_2O$ (7 mL). The mixture was sonicated at room temperature for 1 h. Meanwhile, a precipitate was formed. EtOAc (25 mL) was added and the layers were separated. The organic layer was dried over $Na_2SO_4$ and the solvent was removed in vacuo. The residue was purified by automated column chromatography on the ISCO-companion ($SiO_2$, gradient heptane/EtOAc) to give methyl 2-(5-(3-chloro-4-phenylquinolin-2-yl)thiophen-2-yl)acetate (190 mg, 0.48 mmol, yield 28%) as an off-white solid with an HPLC purity of 98.6%. LC-MS [M+H] 394 ($C_{22}H_{16}ClNO2S+H$, expected 394.1). The $^1$H-NMR spectrum was in accordance with the chemical structure.

Example 18: Preparation of 2-(5-(3-chloro-4-phenylquinolin-2-yl)thiophen-2-yl)acetic acid (Formula Ib-ii)

A mixture of methyl 2-(5-(3-chloro-4-phenylquinolin-2-yl)thiophen-2-yl)acetate (prepared as described in Example 17) (66 mg, 0.168 mmol) in THF (1 mL), MeOH (1 mL) and 2M NaOH (1 mL) was stirred at room temperature for 3 h. Conversion was complete according to TLC and the solvent was evaporated in vacuo. The pH of the aqueous residue was adjusted to 6-7 by addition of 1 M HCl. The mixture was concentrated in vacuo and the residue was purified by automated column chromatography on the ISCO-companion ($SiO_2$, $CH_2Cl_2$/MeOH) to give 2-(5-(3-chloro-4-phenylquinolin-2-yl)thiophen-2-yl)acetic acid (30 mg, 0.079 mmol, yield 47%) as an off-white solid with an HPLC purity of 94.8%. LC-MS [M+H] 380 ($C_{21}H_{14}ClNO_2S+H$, expected 380.04). The $^1$H-NMR spectrum was in accordance with the chemical structure.

Example 19: Preparation of 2-(5-(8-methoxy-4-phenylquinolin-2-yl)thiophen-2yl)acetamide (Formula Ib-v)

A mixture of (2-amino-3-methoxyphenyl)(phenyl)methanone (340 mg, 1.5 mmol), 2-(5-acetylthiophen-2-yl)acetamide (100 mg, 0.546 mmol) and citric acid (153 mg, 0.8 mmol) was heated for 2 d to 120° C. (sandbath). The crude mixture was taken up in ethyl acetate (20 mL) and washed with sat. $NaHCO_3$ (2×10 mL) and dried over $Na_2SO_4$. The solvent was evaporated in vacuo and the residue was purified by repeated automated column chromatography on the ISCO-companion ($SiO_2$, gradient ethyl acetate/heptane) to give 2-(5-(8-methoxy-4-phenylquinolin-2-yl)thiophen-2-yl)acetamide (29 mg, 0.078 mmol, yield 14%) as an tan solid with an HPLC purity of 96.4%. LC-MS [M+H] 375 ($C_{22}H_{18}N_2O_2S+H$, expected 375.1). The $^1$H-NMR spectrum was in accordance with the chemical structure.

Example 20: Preparation of 2-(5-(8-ethyl-4-phenylquinolin-2-yl)thiophen-2-yl)acetamide (Formula Ib-vi)

A mixture of (2-amino-3-ethylphenyl)(phenyl)methanone (112 mg, 0.5 mmol), 2-(5-acetylthiophen-2-yl)acetamide (31 mg, 0.17 mmol) and citric acid (48 mg, 0.25 mmol) was heated for 18 hours to 120° C. (sandbath). The crude mixture was taken up in ethyl acetate (20 mL) and washed with sat. $NaHCO_3$ (10 mL) and brine (10 ml) and dried over $Na_2SO_4$. The solvent was evaporated in vacuo and the residue was purified by automated column chromatography on the ISCO-companion ($SiO_2$, gradient ethyl acetate/heptane) to give 2-(5-(8-ethyl-4-phenylquinolin-2-yl)thiophen-2-yl)acetamide (28 mg, 0.075 mmol, 44%) as a tan solid with an HPLC purity of 98.4%. LC-MS [M+H] 373 ($C_{23}H_{20}N_2OS$+H, expected 373.13). The $^1$H-NMR spectrum was in accordance with the chemical structure.

Example 21: Preparation of methyl 2-(4-(4-phenylquinolin-2-yl)phenoxy)acetate (Formula IIc-i)

A mixture of 2-aminobenzophenone (200 mg, 1.0 mmol), 4'-hydroxyacetophenone (150 mg, 1.1 mmol) and citric acid (96 mg, 0.5 mmol) was heated for 24 hours to 120° C. (sandbath). The crude mixture was taken up in $CH_2Cl_2$ (2 mL): a solid precipitated, which was collected by filtration. After washing with some $CH_2Cl_2$ (2×1 mL), it was dried in air to give 4-(4-phenylquinolin-2-yl)phenol (70 mg, 0.23 mmol, 23%) as an off-white solid. The $^1$H-NMR spectrum was in accordance with the chemical structure.

A mixture of 4-(4-phenylquinolin-2-yl)phenol (70 mg, 0.236 mmol), $K_2CO_3$ (65 mg, 0.47 mmol) and methyl bromoacetate (45 mL, 72 mg, 0.47 mmol) in acetone (10 mL) was refluxed for 18 hours. The mixture was filtered off, the filtrate was rinsed with ethyl acetate (20 mL) and was concentrated in vacuo to give methyl 2-(4-(4-phenylquinolin-2-yl)phenoxy)acetate (84 mg, 0.227 mmol, yield 96%) as an off-white solid with an HPLC purity of 97.6%. LC-MS [M+H] 370 ($C_{24}H_{19}NO_3$+H, expected 370.14). The $^1$H-NMR spectrum was in accordance with the chemical structure.

When introducing elements of the present disclosure, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description shall be interpreted as illustrative and not in a limiting sense.

What is claimed is:

1. A method of controlling fungal pathogens, the method comprising administering to a plant, a seed or soil a composition comprising an effective amount of a compound of Formula II, or a salt thereof,

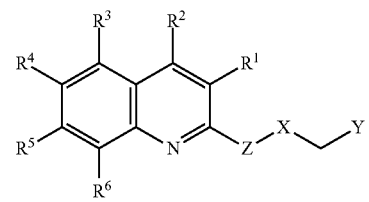

Formula II wherein $R^1$ is selected from the group consisting of hydrogen, halogen, alkyl, alkoxy, haloalkyl, and haloalkoxy;

$R^2$ is selected from the group consisting of aryl and heteroaryl, each of which may be optionally independently substituted with one or more substituents selected from the group consisting of halogen, OH, CN, alkyl, alkoxy, haloalkyl, haloalkoxy, alkenyl, $C_1$ to $C_4$ hydroxyalkyl, $N(R^7R^8)$, and $NR^9C(O)R^{10}$, wherein $R^7$ and $R^8$ are each independently selected from the group consisting of hydrogen and alkyl, and wherein $R^9$ is selected from the group consisting of hydrogen and alkyl and $R^{10}$ is alkyl;

$R^3$, $R^4$, $R^5$, and $R^6$ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl;

X is selected from the group consisting of a bond, $CH_2$, O, S, NH, and $N(CH_3)$;

Y is selected from the group consisting of hydrogen, a prodrug of a carboxylic acid and a carboxylic acid isostere, wherein the prodrug of a carboxylic acid is selected from the group consisting of $CH_2OH$ and $C(O)OR^{11}$, wherein $R^{11}$ is selected from the group consisting of methyl, ethyl, 2-oxopropyl, 2- morpholinoethyl, and pivaloyloxymethyl, and wherein the carboxylic acid isostere is selected from the group consisting of tetrazolyl, aminosulfonyl, acylaminosulfonyl, methylsulfonylcarbamyl, thiazolidinedionyl, oxazolidinedionyl, oxadiazolonyl, $P(O)(OH)_2$, $P(O)(OH)H$, and $SO_3H$; and Z is selected from the group consisting of aryl and heteroaryl, each of which may be optionally independently substituted with one or more substituents selected from the group consisting of halogen, alkyl, alkoxy, haloalkyl, haloalkoxy, $C_1$ to $C_4$ hydroxyalkyl, CN, and C(H)O, with the proviso that when $R^2$ is phenyl, Z is phenyl, and Y is $C(O)OCH_2CH_3$, $R^4$ is other than halogen.

2. The method of claim 1 wherein the compound is of Formula IIa or a salt thereof, Formula IIa

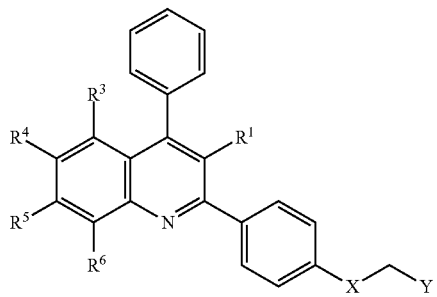

wherein
- R¹ is selected from the group consisting of hydrogen, halogen, alkyl, alkoxy, haloalkyl, and haloalkoxy;
- R³, R⁴, R⁵, and R⁶ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl;
- X is selected from the group consisting of $CH_2$, O, S, NH, and $N(CH_3)$; and
- Y is selected from the group consisting of hydrogen and a carboxylic acid isostere, wherein the carboxylic acid isostere is selected from the group consisting of tetrazolyl, aminosulfonyl, acylaminosulfonyl, methylsulfonylcarbamyl, thiazolidinedionyl, oxazolidinedionyl, oxadiazolonyl, $P(O)(OH)_2$, $P(O)(OH)H$, and $SO_3H$.

3. The method of claim 1 wherein the compound is of Formula IIb or a salt thereof, Formula IIb

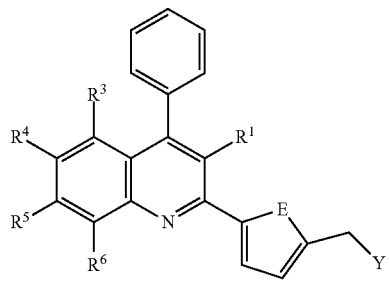

wherein
- R¹ is selected from the group consisting of hydrogen, halogen, alkyl, alkoxy, haloalkyl, and haloalkoxy;
- R³, R⁴, R⁵, and R⁶ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R_7$ and $R^8$ are each independently selected from the group consisting of hydrogen and alkyl, and wherein $R^9$ is selected from the group consisting of hydrogen and alkyl and $R^{10}$ and $R^{11}$ are alkyl;
- Y is a carboxylic acid isostere selected from the group consisting of tetrazolyl, aminosulfonyl, acylaminosulfonyl, methylsulfonylcarbamyl, thiazolidinedionyl, oxazolidinedionyl, oxadiazolonyl, $P(O)(OH)_2$, $P(O)(OH)H$, and $SO_3H$; and
- E is selected from the group consisting of S, O, and $N(CH_3)$.

4. The method of claim 1 wherein the compound is of Formula IIc or a salt thereof, Formula IIc

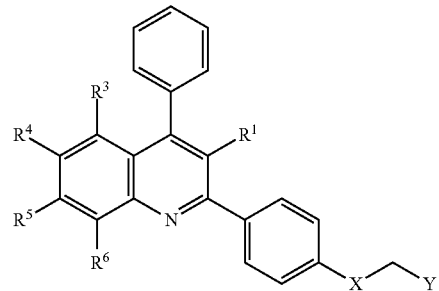

wherein
- R¹ is selected from the group consisting of hydrogen, halogen, alkyl, alkoxy, haloalkyl, and haloalkoxy;
- R³, R⁴, R⁵, and R⁶ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl;
- X is selected from the group consisting of $CH_2$, O, S, NH, and $N(CH_3)$; and
- Y is selected from the group consisting of hydrogen and a prodrug of carboxylic acid, wherein the prodrug of a carboxylic acid is selected from the group consisting of $CH_2OH$ and $C(O)OR^{11}$, wherein $R^{11}$ is selected from the group consisting of methyl, ethyl, 2-oxopropyl, 2-morpholinoethyl, and pivaloyloxymethyl; with the proviso that when Y is $C(O)OCH_2CH_3$, $R^4$ is other than halogen.

5. The method of claim 1 wherein the compound is of Formula IId or a salt thereof, Formula IId

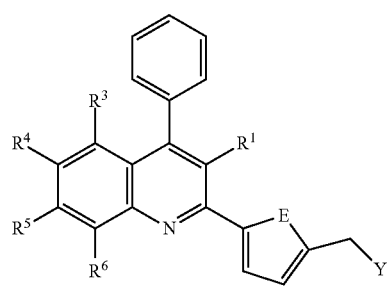

wherein
- R¹ is selected from the group consisting of hydrogen, halogen, alkyl, alkoxy, haloalkyl, and haloalkoxy;
- R³, R⁴, R⁵, and R⁶ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl;

Y is a prodrug of carboxylic acid, wherein the prodrug of a carboxylic acid is selected from the group consisting of $CH_2OH$ and $C(O)OR^{11}$, wherein $R^{11}$ is selected from the group consisting of methyl, ethyl, 2-oxopropyl, 2-morpholinoethyl, and pivaloyloxymethyl; and E is selected from the group consisting of S, O, and $N(CH_3)$.

6. The method of claim 1 wherein $R^2$ is phenyl.

7. The method of claim 1 wherein Z is selected from the group consisting of phenyl and thienyl.

8. The method of claim 1 wherein $R^1$ is hydrogen.

9. The method of claim 1 wherein the method comprises administering the composition to a seed.

10. A treated seed prepared according to the method of claim 9.

11. The method of claim 1 wherein the method comprises exogenously administering the composition to a plant.

12. The method of claim 1 wherein the compound is of Formula IIb or a salt thereof,

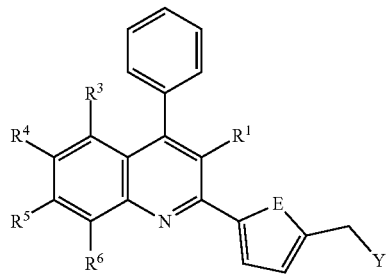

Formula IIb wherein $R^1$ is selected from the group consisting of hydrogen, halogen, alkyl, alkoxy, haloalkyl, and haloalkoxy;

$R^3$, $R^4$, $R^5$, and $R^6$ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl;

Y is a carboxylic acid isostere selected from the group consisting of tetrazolyl, aminosulfonyl, acylaminosulfonyl, methylsulfonylcarbamyl, thiazolidinedionyl, oxazolidinedionyl, oxadiazolonyl, $P(O)(OH)_2$, $P(O)(OH)H$, and $SO_3H$; and E is selected from the group consisting of S, O, and $N(CH_3)$.

13. A method of modulating acetyl-CoA carboxylase (ACCase) in a biological organism, the method comprising administering to the biological organism a composition comprising an effective amount of a compound of Formula II or a salt thereof,

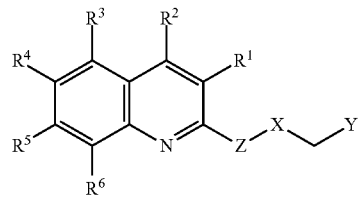

Formula II wherein $R^1$ is selected from the group consisting of hydrogen, halogen, alkyl, alkoxy, haloalkyl, and haloalkoxy;

$R^2$ is selected from the group consisting of aryl and heteroaryl, each of which may be optionally independently substituted with one or more substituents selected from the group consisting of halogen, OH, CN, alkyl, alkoxy, haloalkyl, haloalkoxy, alkenyl, $C_1$ to $C_4$ hydroxyalkyl, $N(R^7R^8)$, and $NR^9C(O)R^{10}$, wherein $R^7$ and $R^8$ are each independently selected from the group consisting of hydrogen and alkyl, and wherein $R^9$ is selected from the group consisting of hydrogen and alkyl and $R^{10}$ is alkyl;

$R^3$, $R^4$, $R^5$, and $R^6$ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl;

X is selected from the group consisting of a bond, $CH_2$, O, S, NH, and $N(CH_3)$;

Y is selected from the group consisting of hydrogen, a prodrug of a carboxylic acid and a carboxylic acid isostere, wherein the prodrug of a carboxylic acid is selected from the group consisting of $CH_2OH$ and $C(O)OR^{11}$, wherein $R^{11}$ is selected from the group consisting of methyl, ethyl, 2-oxopropyl, 2-morpholinoethyl, and pivaloyloxymethyl, and wherein the carboxylic acid isostere is selected from the group consisting of tetrazolyl, aminosulfonyl, acylaminosulfonyl, methylsulfonylcarbamyl, thiazolidinedionyl, oxazolidinedionyl, oxadiazolonyl, $P(O)(OH)_2$, $P(O)(OH)H$, and $SO_3H$; and Z is selected from the group consisting of aryl and heteroaryl, each of which may be optionally independently substituted with one or more substituents selected from the group consisting of halogen, alkyl, alkoxy, haloalkyl, haloalkoxy, $C_1$ to $C_4$ hydroxyalkyl, CN, and C(H)O, with the proviso that when $R^2$ is phenyl, Z is phenyl, and Y is $C(O)OCH_2CH_3$, $R^4$ is other than halogen.

14. The method of claim 13 wherein the compound is of Formula IIa or a salt thereof, Formula IIa wherein
R¹ is selected from the group consisting of hydrogen, halogen, alkyl, alkoxy, haloalkyl, and haloalkoxy;
R³, R⁴, R⁵, and R⁶ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl;
X is selected from the group consisting of $CH_2$, O, S, NH, and $N(CH_3)$; and
Y is selected from the group consisting of hydrogen and a carboxylic acid isostere, wherein the carboxylic acid isostere is selected from the group consisting of tetrazolyl, aminosulfonyl, acylaminosulfonyl, methylsulfonylcarbamyl, thiazolidinedionyl, oxazolidinedionyl, oxadiazolonyl, $P(O)(OH)_2$, $P(O)(OH)H$, and $SO_3H$.

15. The method of claim 13 wherein the compound is of Formula IIc or a salt thereof, Formula IIc wherein
R¹ is selected from the group consisting of hydrogen, halogen, alkyl, alkoxy, haloalkyl, and haloalkoxy;
R³, R⁴, R⁵, and R⁶ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl;
X is selected from the group consisting of $CH_2$, O, S, NH, and $N(CH_3)$; and
Y is selected from the group consisting of hydrogen and a prodrug of carboxylic acid, wherein the prodrug of a carboxylic acid is selected from the group consisting of $CH_2OH$ and $C(O)OR^{11}$, wherein $R^{11}$ is selected from the group consisting of methyl, ethyl, 2-oxopropyl, 2-morpholinoethyl, and pivaloyloxymethyl;
with the proviso that when Y is $C(O)OCH_2CH_3$, $R^4$ is other than halogen.

16. The method of claim 13 wherein the compound is of Formula IId or a salt thereof, Formula IId wherein
R¹ is selected from the group consisting of hydrogen, halogen, alkyl, alkoxy, haloalkyl, and haloalkoxy;
R³, R⁴, R⁵, and R⁶ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl;
Y is a prodrug of carboxylic acid, wherein the prodrug of a carboxylic acid is selected from the group consisting of $CH_2OH$ and $C(O)OR^{11}$, wherein $R^{11}$ is selected from the group of consisting methyl, ethyl, 2-oxopropyl, 2-morpholinoethyl, and pivaloyloxymethyl; and
E is selected from the group consisting of S, O, and $N(CH_3)$.

17. The method of claim 13 wherein $R^2$ is phenyl.
18. The method of claim 13 wherein Z is selected from the group consisting of phenyl and thienyl.
19. The method of claim 13 wherein $R^1$ is hydrogen.
20. The method of claim 13 wherein the method comprises administering the composition to a seed.
21. The method of claim 13 wherein the method comprises exogenously administering the composition to a plant.
22. A compound of Formula II or salt thereof Formula II wherein
R¹ is selected from the group consisting of hydrogen, halogen, alkyl, alkoxy, haloalkyl, and haloalkoxy;
R² is selected from the group consisting of aryl and heteroaryl, each of which may be optionally independently substituted with one or more substituents selected from the group consisting of halogen, OH, CN, alkyl, alkoxy, haloalkyl, haloalkoxy, alkenyl, $C_1$ to $C_4$ hydroxyalkyl, $N(R^7R^8)$, and $NR^9C(O)R^{10}$, wherein $R^7$ and $R^8$ are each independently selected from the group consisting of hydrogen and alkyl, and wherein $R^9$ is selected from the group consisting of hydrogen and alkyl and $R^{10}$ is alkyl;

$R^3$, $R^4$, $R^5$, and $R^6$ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl;

X is selected from the group consisting of a bond, $CH_2$, O, S, NH, and $N(CH_3)$;

Y is selected from the group consisting of hydrogen, a prodrug of a carboxylic acid and a carboxylic acid isostere, wherein the prodrug of a carboxylic acid is selected from the group consisting of $CH_2OH$ and $C(O)OR^{11}$, wherein $R^{11}$ is selected from the group consisting of methyl, ethyl, 2-oxopropyl, 2-morpholinoethyl, and pivaloyloxymethyl, and wherein the carboxylic acid isostere is selected from the group consisting of tetrazolyl, aminosulfonyl, acylaminosulfonyl, methylsulfonylcarbamyl, thiazolidinedionyl, oxazolidinedionyl, oxadiazolonyl, $P(O)(OH)_2$, $P(O)(OH)H$, and $SO_3H$; and Z is selected from the group consisting of aryl and heteroaryl, each of which may be optionally independently substituted with one or more substituents selected from the group consisting of halogen, alkyl, alkoxy, haloalkyl, haloalkoxy, $C_1$ to $C_4$ hydroxyalkyl, CN, and C(H)O, with the proviso that when $R^2$ is phenyl, Z is phenyl, and Y is $C(O)OCH_2CH_3$, $R^4$ is other than halogen.

23. The compound of claim 22 wherein the compound is of Formula IIa or a salt

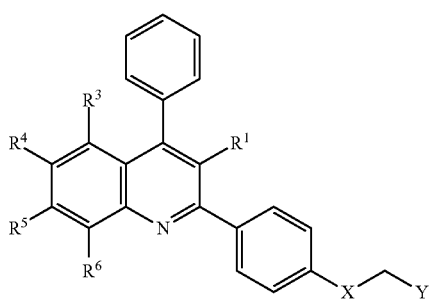

Formula IIa wherein
  $R^1$ is selected from the group consisting of hydrogen, halogen, alkyl, alkoxy, haloalkyl, and haloalkoxy;
  $R^3$, $R^4$, $R^5$, and $R^6$ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl;

X is selected from the group consisting of $CH_2$, O, S, NH, and $N(CH_3)$; and

Y is selected from the group consisting of hydrogen and a carboxylic acid isostere, wherein the carboxylic acid isostere is selected from the group consisting of tetrazolyl, aminosulfonyl, acylaminosulfonyl, methylsulfonylcarbamyl, thiazolidinedionyl, oxazolidinedionyl, oxadiazolonyl, $P(O)(OH)_2$, $P(O)(OH)H$, and $SO_3H$.

24. The compound of claim 22 wherein the compound is of Formula IIb or a salt thereof,

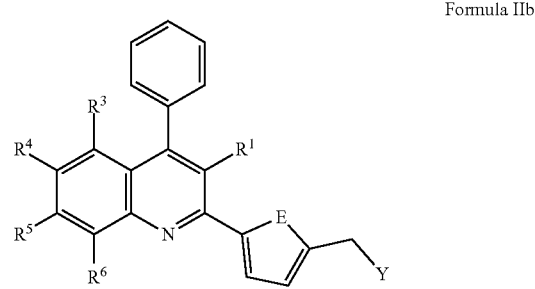

Formula IIb wherein
  $R^1$ is selected from the group consisting of hydrogen, halogen, alkyl, alkoxy, haloalkyl, and haloalkoxy;
  $R^3$, $R^4$, $R^5$, and $R^6$ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl;

Y is a carboxylic acid isostere selected from the group consisting of tetrazolyl, aminosulfonyl, acylaminosulfonyl, methylsulfonylcarbamyl, thiazolidinedionyl, oxazolidinedionyl, oxadiazolonyl, $P(O)(OH)_2$, $P(O)(OH)H$, and $SO_3H$; and E is selected from the group consisting of S, O, and $N(CH_3)$.

25. The compound of claim 22 wherein the compound is of Formula IIc or a salt thereof,

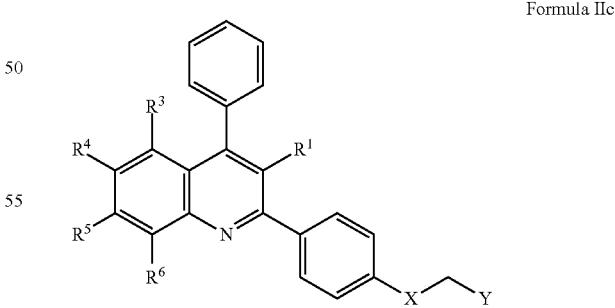

Formula IIc wherein
  $R^1$ is selected from the group consisting of hydrogen, halogen, alkyl, alkoxy, haloalkyl, and haloalkoxy;
  $R^3$, $R^4$, $R^5$, and $R^6$ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl;

X is selected from the group consisting of $CH_2$, O, S, NH, and $N(CH_3)$; and

Y is selected from the group consisting of hydrogen and a prodrug of carboxylic acid, wherein the prodrug of a carboxylic acid is selected from the group consisting of $CH_2OH$ and $C(O)OR^{11}$, wherein $R^{11}$ is selected from the group consisting of methyl, ethyl, 2-oxopropyl, 2-morpholinoethyl, and pivaloyloxymethyl;

with the proviso that when Y is $C(O)OCH_2CH_3$, $R^4$ is other than halogen.

26. The compound of claim 22 wherein the compound is of Formula IId or a salt thereof,

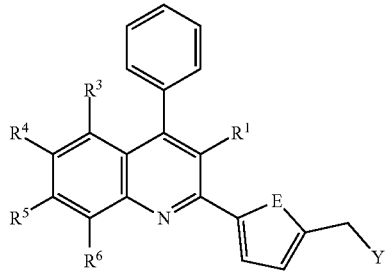

Formula IId wherein $R^1$ is selected from the group consisting of hydrogen, halogen, alkyl, alkoxy, haloalkyl, and haloalkoxy;

$R^3$, $R^4$, $R^5$, and $R^6$ are each independently selected from the group consisting of hydrogen, halogen, OH, alkyl, alkoxy, haloalkyl, haloalkoxy, $C_1$ to $C_4$ hydroxyalkyl, $N(R^7R^8)$, $NR^9C(O)R^{10}$, and $C(O)R^{11}$, wherein $R^7$ and $R^8$ are each independently selected from the group consisting of hydrogen and alkyl, and wherein $R^9$ is selected from the group consisting of hydrogen and alkyl and $R^{10}$ and $R^{11}$ are alkyl;

Y is a prodrug of carboxylic acid, wherein the prodrug of a carboxylic acid is selected from the group consisting of $CH_2OH$ and $C(O)OR^{11}$, wherein $R^{11}$ is selected from the group consisting of methyl, ethyl, 2-oxopropyl, 2-morpholinoethyl, and pivaloyloxymethyl; and E is selected from the group consisting of S, O, and $N(CH_3)$.

27. The compound of claim 22 wherein $R^2$ is phenyl.

28. The compound of claim 22 wherein Z is selected from the group consisting of phenyl and thienyl.

29. The compound of claim 22 wherein $R^1$ is hydrogen.

* * * * *

UNITED STATES PATENT AND TRADEMARK OFFICE
CERTIFICATE OF CORRECTION

Page 1 of 1

PATENT NO. : 10,995,070 B2
APPLICATION NO. : 16/239946
DATED : May 4, 2021
INVENTOR(S) : Slomczynska et al.

It is certified that error appears in the above-identified patent and that said Letters Patent is hereby corrected as shown below:

In the Claims

Column 65, Claim 3, Line 58: "$N(R^7R^8)$, $NR^9C(O)R^{10}$, and $C(O)R^{11}$, wherein $R_7$ and"
Should read -- $N(R^7R^8)$, $NR^9C(O)R^{10}$, and $C(O)R^{11}$, wherein $R^7$ and --

Column 71, Claim 23, Line 41: "of Formula IIa or a salt"
Should read -- of Formula IIa or a salt thereof, --

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*